US008038999B2

(12) United States Patent
Sirbasku

(10) Patent No.: US 8,038,999 B2
(45) Date of Patent: Oct. 18, 2011

(54) BREAST CANCER ERADICATION PROGRAM

(76) Inventor: David A. Sirbasku, Houston, TX (US)

(*) Notice: Subject to any disclaimer, the term of this patent is extended or adjusted under 35 U.S.C. 154(b) by 60 days.

(21) Appl. No.: 11/946,190

(22) Filed: Nov. 28, 2007

(65) Prior Publication Data
US 2010/0278729 A9 Nov. 4, 2010

Related U.S. Application Data

(63) Continuation of application No. 10/293,019, filed on Nov. 13, 2002, now abandoned, which is a continuation-in-part of application No. 09/852,958, filed on May 10, 2001, and a continuation-in-part of application No. 09/852,547, filed on May 10, 2001.

(60) Provisional application No. 60/338,037, filed on Nov. 13, 2001, provisional application No. 60/231,273, filed on Sep. 8, 2000, provisional application No. 60/229,071, filed on Aug. 30, 2000, provisional application No. 60/208,111, filed on May 31, 2000, provisional application No. 60/208,348, filed on May 31, 2000, provisional application No. 60/203,314, filed on May 10, 2000.

(51) Int. Cl.
A61K 33/26 (2006.01)
A61P 35/00 (2006.01)

(52) U.S. Cl. .............. 424/155.1; 424/1.61; 424/646

(58) Field of Classification Search .............. 424/155.1, 424/1.61, 645
See application file for complete search history.

(56) References Cited

U.S. PATENT DOCUMENTS

| 4,393,071 A | 7/1983 | Fujii et al. |
| 4,683,200 A | 7/1987 | Hirohashi et al. |
| 4,859,585 A | 8/1989 | Sonnenschein et al. |
| 5,075,425 A | 12/1991 | Kotitschke et al. |
| 5,135,849 A | 8/1992 | Soto |
| 6,200,547 B1 | 3/2001 | Volkonsky et al. |
| 2002/0006630 A1 | 1/2002 | Sirbasku |

FOREIGN PATENT DOCUMENTS

| EP | 0246734 | 11/1987 |
| EP | 0702960 A1 | 3/1996 |
| WO | WO 9213563 | 8/1992 |
| WO | WO 9640108 | 12/1996 |
| WO | 99/33869 | 7/1999 |

OTHER PUBLICATIONS

Sato (Nippon Gan Chiryo Gakkaishi 28(10):1716-1723 (1993).*
Reddel et al (Exp. Cell Research 161:277-284 (1985)).*
Wang et al. (Anticancer Research 19:445-450 (1999)).*
Jiang et al (Anticancer Research 22:2685-2692 (2002)).*
Mathias et al (J. Nuclear Medicine 37(6):1003-1008 (1996).*
Murphy (The Oncologist 3:129-130 (1998).*
Patel et al. (Proc. Nat'l. Acad. Sci. 80:6518-6522 (1983).*
Feng et al. (Journal Dairy Science 78:2352-2357 (1995).*
Hallaway et al (Proc. Nat'l. Acad. Sci. 85:10108-10112 (1989).*
Larson et al (J. Nat'l. Cancer Inst. 64(1): 41-53 (1980).*
Kresse et al (Magnetic Resonance in Medicine 40(2):236-242 (1998).*
Schirner et al. (J. Can. Res. Clin. Oncol. 121: Suppl. 1, A2 Jan. 1995; Abstract).*
Danielpour et al., In Vitro Cell. & Dev. Biol. Jan. 1988, 24, pp. 42-52.
Parisot et al., British Journal of Cancer, 1999, vol. 79(5/6), pp. 693-700.
Deture et al., A Comparison of Serum Immunoglobulins From Patients With Non-Neoplastic Prostates and Prostatic Carcinoma, The Journal of Urology, Oct. 1978, pp. 435-437, vol. 120.
O'Boyle et al., Immunization of Colorectal Cancer Patients with Modified Ovine Submaxillary Gland Mucin and Adjuvants Induces IgM and IgG Antibodies to Sialylated Tn, Cancer Research, Oct. 15, 1992, pp. 5663-5667, vol. 52.
Schauenstein et al., Selective Decrease in Serum Immunoglobulin G1, American Cancer Society, Aug. 1, 1996, pp. 511-516, vol. 78, Issue No. 3.
Patent Application Search Report date mailed Mar. 3, 2006 from European Patent Application No. 02780675.1-2123.
Furuya et al (Cancer Research, Dec. 1989, vol. 49, pp. 6670-6674).
Hoffman ('The Biochemistry of Clinical Medicine', 1970, pp. 48 and 55).
European Search Report Dated Feb. 2, 2011.
European Search Report Dated Feb. 4, 2011.
Karmanos Cancer Center website search ("MCF-7"; Apr, 20, 2010; pp. 1-2).
Kemp et al, Effects of Anti-Transferrin Receptor Antibodies on the Growth of Neoplastic Cells, Pathobiology, Karger, Basel, CH, vol. 60, No. 1, Jan. 1, 1992, pp. 27-32.
Kontoghiorghes et al, Site Specificity of Iron Removal From Transferrin by Alpha-Keohydroxypyridine Chelators, Febs Letters, Elsevier, Ambsterdam, NL, vol. 189, No. 1, Sep. 9, 1985, pp. 141-144.
Yang et al., An Antisense Transferrin Receptor Oligonucleotide Suppresses Gene Expression and Proliferation in Human Breast Cancer Cell Lines; Proceedings of the 89th Annual Meeting of The American Asociation for Cancer Research, New Orleans, LA, Mar. 28-Apr. 1, 1988, vol. 39, p. 417/418.
Yang et al., Antisense Transferrin Receptor Oligonucleotide Induces Apoptosis in Human MCF-7 Breat Carcinoma Cells; Proceedings of the Annual Meeting of The American Association for Cancer Research, vol. 41, Mar. 1, 2000, p. 752.
Yang et al., Expression of Transferrin Receptor and Ferritin H-Chain MRNA Are Associated with Clinical and Histopathological Prognostic Indicators in Breast Cancer, International Institute of Anticancer Research, vol. 21, No. 1B, Jan. 1, 2001, pp. 541-550.

* cited by examiner

Primary Examiner — Lynn Bristol
(74) Attorney, Agent, or Firm — Merchant & Gould P.C.

(57) ABSTRACT

A method of treating breast cancer that is at least partially ER+ is disclosed. The method comprises administering at a tumor site in a mammalian subject a pharmaceutically acceptable form of Fe(II) or Fe(III) in a suitable carrier. A four-part program aimed at eradicating breast cancer includes (a) local treatment and prevention of spread from a contained breast site, preferably using local administration of a ferric iron composition, (b) treatment of disseminated (metastatic) breast cancer, (c) reduction in the risk of developing breast cancer, preferably by enhancing dimeric/polymeric IgA and polymeric IgM inhibition of estrogen responsive cell growth, and (d) protection against cancer causing agents.

36 Claims, No Drawings

BREAST CANCER ERADICATION PROGRAM

CROSS-REFERENCE TO RELATED APPLICATIONS

This application is a continuation of U.S. patent application Ser. No. 10/293,019 filed Nov. 13, 2002, which in turn claims the benefit under 35 U.S.C. §119(e) of U.S. Provisional Patent Application No. 60/338,037 filed Nov. 13, 2001, and is a continuation-in-part of U.S. patent application Ser. Nos. 09/852,958 and 09/852,547, both filed May 10, 2001, the disclosures of each of which are hereby incorporated herein by reference.

STATEMENT REGARDING FEDERALLY SPONSORED RESEARCH OR DEVELOPMENT

Research leading to the present invention was supported in part by the federal government under Grant Nos. DAMD17-94-J-4473, DAMD17-98-1-8337 and DAMD17-99-1-9405 awarded by the Defense Department through the US Army Medical Research and Materiel Command, Breast Cancer Research Program. The United States government may have certain rights in the invention.

BACKGROUND OF THE INVENTION

1. Field of the Invention

The present invention generally relates to methods and compositions for the eradication of cancers of the mucosal endothelial tissues. More particularly, the present invention relates to the use of such compositions and methods for breast cancer risk reduction, prevention and treatment.

2. Description of Related Art

For women with breast cancer, the term "eradication" has different meanings depending upon the state of their disease. Additionally, for women still disease free, eradication means preventing the development of breast cancer. Today, there are no known preventions for breast cancer. Although many risk factors have been identified for breast cancer (76-78), reduction of overall risk from the current United States level of one-in-eight has not been achieved short of the use of the anti-estrogen tamoxifen as a preventative (79). However tamoxifen is only for use by very high-risk women (79). It is not for use with the general population, both because of adverse side effects and because of disruption of reproductive capacity. Accordingly, tamoxifen is under evaluation for high-risk women, but is not considered appropriate for use as a standard preventative due to its serious side-effects and causation of a number of endocrine problems. Treatment with tamoxifen for more than five years may in fact induce breast cancer. It is now recommended that this therapy be limited to only five years. This does not cover the span of a women's lifetime. Based on knowledge today, it may be possible to reduce risk by alterations of life style and diet, but these are at best fractional gains and offer no assurances. Even women who lead very health-risk conscious lives still develop breast cancer. A successful mass prevention is a primary goal in the fight against this disease.

For women diagnosed with breast cancer, the current most effective eradication methods begin with various surgical procedures (i.e. mastectomy or breast conservation surgery or more commonly lumpectomy). Without doubt, removing a primary tumor is an effective first step of eradication provided tumor cells have not escaped to other body sites. Given that we understand that escape is a possibility, or that multiple unrecognized tumor foci are present in one or both breasts, many breast cancer patients opt for radiation therapy, adjuvant chemotherapy and/or tamoxifen treatment even when they are diagnosed as node negative. The term "node negative" indicates that cancer cells have not moved to the axillary nodes from the breast. Commonly however, it is thought useful to "shrink" primary tumors before surgical removal. Today this is done by systemic chemotherapy or radiation therapy. Patients with node negative estrogen receptor positive ($ER^+$) breast cancer may also be treated with anti-estrogen (e.g. tamoxifen) as is often done for postmenopausal women. Depending upon age and physical condition, anti-estrogen therapy is now a common alternative for many postmenopausal women.

For breast cancer patients who are axillary node positive (either $ER^+$ or $ER^-$), additional treatment is essential including those noted above. There is no doubt that these modalities have a major positive impact on long term survival, but it is likewise clear to basic cancer investigators and cancer clinicians alike that the failure rate is significant even despite frequent quoting of favorable statistical data. Currently, node positive women without other evidence of dissemination can be treated by standard chemotherapy and/or radiation therapy. However, node positive patients with $ER^-$ tumors are at risk no matter the therapy utilized. For these women, the use of anti-hormone therapy is not as effective as with patients with $ER^+$ tumors.

It is with the diagnosis of metastases to liver, bone, brain, lung, etc., that another more serious level of the eradication issues arises, and standard chemotherapy is most often not effective. For reasons both known and unknown, these cases have a very poor prognosis. Current chemotherapy can sometimes retard metastatic cancer growth, but as cancers spread they become progressively more therapy resistant. The level of public concern about this issue is clear from anticipation of the benefits of such new drugs as Herceptin®, which is a monoclonal antibody against the HER2 receptor. Introduction of Herceptin® was accompanied by widespread reports in the news media that heightened expectations. Unfortunately, even this new family of biopharmaceuticals is not an effective means of eradication. At best, Herceptin® provides only a small increase in survival time and then only in combination with chemotherapy and only with a minority of treated patients (70). While other types of drugs are under investigation, the magnitude of the disseminated cancer problem remains undiminished.

Iron deprivation has been discussed as a means of eliminating cancer cells (39,40), but the focus has been on two technologies that, used alone, have not worked. First, those investigators have considered iron deprivation via treatment with chelators that bind the metal and thereby render it metabolically inactive. Chelation alone has not removed enough iron from the body to be effective as an anticancer program (41). This is to be expected, for it is known that iron is retained in organs and tissues with a biological half-life of about 2000 days. Most likely, chelation alone will not be an effective therapy.

Currently, the primary effort in breast cancer research aimed at eradication of the disease is intensely focused by powerful technology that permits identification of a large number of genes, and by the human genome project that promises to solve the cancer problem. To date, these technologies have provided valuable information but have failed to move to the next level of application, cancer eradication.

A brief historical overview of breast cancer research over the past four decades points to numerous periods of advancement, each with its own promise of defeating cancer. For example, during the 1960s investigators were encouraged by newly identified enzyme and metabolic changes in cancer cells. It then seemed clear that these changes were the cause of cancer and that its end was near. During the 1970s, the beginnings of molecular biology (then called microbial genetics) yielded new found information that was thought certain to lead to the end of many human diseases, including cancer. Investigations in the field of endocrine cancer research, during the 1980s, focused on how hormones caused cell growth and developed animal models to study hormone dependent cancer. At that time, serum-free defined animal cell culture was being developed (1) and new substances called growth factors were being explored (2). Also during that period, another major advancement was the discovery of the estrogen receptor (ER) and the hypothesis that it alone controlled estrogen dependent cell growth (3-5). Some investigators did not accept all of the ER hypothesis (6-8), however, and thought that estrogen-inducible growth factors (estromedins) were necessary (6,9,10). It appeared clear at that time that growth factor research would untangle the cancer enigma. Today cancer scientists know this is not the case.

Along with the growth factor research came the "oncogene" explosion of the 1990s, which promised an end to cancer. Today, cancer investigators are inundated by scores of gene changes in cancer. The list grows weekly. A GENBANK search of "breast cancer hot spots" yielded more than 100 "hits" on several chromosomes. This cornucopia of genetic information obscures two facts: First, very few breast cancers can be traced to germ line DNA changes (11). Most are not inherited. Notable exceptions are BRCA1 and BRCA2, which represent at most 1-10% of breast cancers in the United States (31-33). Given that the incidence of breast cancer now approaches 1 in 8, the majority of breast cancers have other origins. Second, sophisticated new molecular technology has identified changes in expression of at least 100 mRNAs in breast cancer cells (11). There is promise of hundreds of gene/expression changes (11-13). It is very unlikely they are all causative or even critical to breast cancer. The tempting scenario is to investigate each mRNA or gene to define its role. Of course, this represents years of work for researchers, and still leaves open the question: "Will this lead to breast cancer eradication"?

It is known that eighty percent or more of breast cancers are invasive ductal carcinomas that arise from ductal cells (85,86) or precursors of ductal cells (85,87). Based on the current state of knowledge, there is no genetic lesion to explain the 70% of breast cancers now termed "sporadic". Certainly the BRCA1 and BRCA2 genes are responsible for at most a small percentage of breast cancers in this country (88-91). Lesions in the p53 gene were initially thought to be important in as many as 15 to 50% of breast cancers (92-94). However, it was far from clear which mutations are causally related to breast cancer onset or which actually constitute secondary changes leading to loss of function of this tumor suppressor gene in the different types of breast cancer (i.e. $ER^+$ or $ER^-$). A more recent study has rightly pointed out the confusion regarding p53 mutations and breast cancer patients (96). Studies of p53 mutations have yielded a wide range of results depending upon the methods employed (97). One useful fact is that the results average about 30 to 40% for loss of heterozygosity at the p53 gene (97). This means the remaining gene may be a "hot spot" (i.e., a chromosomal loci or gene that is frequently altered in breast cancer specimens). However, at this time, there is not sufficient evidence to support the use of p53 as a guide to selection of therapy modalities for breast cancer (98).

In fact, today it is very difficult to explain the great many mutations and other types of genetic expression alterations that are known in breast cancer cells (11). Based on the findings with breast and other types of mucosal cancers, such changes include mutations, translocations, amplifications of oncogenes, loss of heterozygosity (LOH), and allelic imbalances (12,13,100-102). How do all of these happen? Are environmental carcinogens in such high abundance that they explain these data? Despite the concentrated focus given to environmental carcinogens as causes of breast cancer (20,95, 99), that hypothesis has failed to move forward to the level of accepted scientific fact. Ways to reduce the risk of developing breast cancer, ways of preventing its occurrence, and ways to treat existing cases of localized and metastatic breast cancer are urgently needed. Even with the very best of treatments currently available, a longer-term plan is still needed in which prevention is the first line of eradication. A successful prevention will be, preferably, safe and have low or negligible side effects. It should be capable of reducing risk for the majority of women, independent of their economic circumstances. It should cause little or no disruption of life-style or reproductive capacity.

SUMMARY OF PREFERRED EMBODIMENTS

While continued gene searching may not lead to the goal of eradication of breast cancer in the near or even mid-range future, the present invention offers eradication technology that can be applied today—no matter how many gene changes are ultimately associated with cancer development. Eradication is approached from a unique perspective based on discoveries described in more detail below and in co-pending U.S. patent application Ser. No. 09/852,547 entitled "Compositions and Methods for the Diagnosis, Treatment and Prevention of Steroid Hormone Responsive Cancers" and Ser. No. 09/852,958 entitled "Compositions and Methods for Demonstrating Secretory Immune System Regulation of Steroid Hormone Responsive Cancer Cell Growth", and in corresponding International Patent Applications PCT/US01/15171 (WO 01/86307 and PCT/US01/15183 (WO 01/85210), also identified in the list of References, below, as items 29 and 30, and hereby incorporated herein by reference).

The present invention specifically focuses on the eradication of breast cancer, and overcomes many of the problems and barriers in breast cancer research today. In certain embodiments of the invention, (ferric) iron-based treatment of local breast cancer tumors and lumpectomy sites is provided. New treatment strategies for three conditions are disclosed, which include (i) treatment of mastectomy sites to eliminate residual cancer cells, (ii) treatment of primary tumors before surgery, (iii) treatment of the surgical margins of mastectomy sites to eliminate undetected residual cancer cells.

In certain embodiments of the invention, treatment of disseminated/metastatic breast cancer is addressed from a cell nutrition perspective. Both $ER^+$ and $ER^-$ metastatic breast cancers are highly growth dependent upon diferric transferrin as a source of metabolic iron required for cell growth (29,30, 71,72) and more specifically DNA synthesis (73,74), as described in the above cited USPTO pending patent applications, using newly developed serum-free medium cell culture methods. Because of this strict requirement for diferric transferrin, manipulation of iron metabolism is employed to kill disseminated cancer cells.

In certain embodiments of the invention, risk reduction via oral "immunization" is provided, i.e., oral administration of immunogens that result in increased content of secretory immunoglobulins (IgA and IgM) in breast tissue. This approach to risk reduction is based on the very well established fact that DNA synthesis (i.e. cell replication) is required to achieve the full effects of mutagens (80-85). The secretory immunoglobulins IgA and IgM are inhibitors of breast cell DNA synthesis (29,30) and therefore reduce the probability of mutations that lead to breast cancer later in life.

Certain embodiments of the present invention provide methods for eradicating breast cancer by conventional oral or standard immunization against bacteria or other microorganisms existing in the breast duct system that release or cause formation of mutagenic agents that lead to causative genetic changes in the exposed ductal cells. This approach addresses the problem of what single source might give rise to a process that can cause so many mutations and different genetic changes that accumulate over the known prolonged period required to develop breast cancer. Identification of the causative bacteria/microorganisms makes possible the exploitation of the body's secretory immune system to develop secretory immunity or to use standard immunization to transmit immunity to the ductal fluids. Protection from the underlying causative agents will provide the best means of ultimate eradication of breast cancer. A microbial origin of breast cancer does not appear to have been previously described or suggested in the scientific literature.

In preferred embodiments of the present invention, all four parts of the breast cancer eradication program are applied to appropriate groups of affected or at-risk individuals, including (1) local treatment and prevention of spread from a contained breast site; (2) treatment of disseminated (metastatic) breast cancer; (3) reduction in the risk of developing breast cancer; and (4) protection against cancer causing agents. In some embodiments, one or more parts of the program are employed for treatment, reduction of risk, or prevention of breast cancer in a single individual or a one or more groups of individuals. Full implementation of the preferred four-part integrated program is expected to eradicate breast cancer within the next decade. These and other embodiments, features and advantages of the present invention will become apparent with reference to the following description.

DETAILED DESCRIPTION OF PREFERRED EMBODIMENTS

The breakthrough in breast cancer research disclosed in U.S. patent application Ser. Nos. 09/852,958 and 09/852,547, and which also applies to cancers of other mucosal epithelial tissues in the body, is further implemented and extended herein. The disclosures of those applications are hereby incorporated herein by reference. Purification of new "serum factor(s)" that regulate estrogen responsive breast cancer cell growth in culture is described in those preceding applications. The purification yielded dimeric/polymeric immunoglobulin A (IgA) and pentameric immunoglobulin M (IgM) as the active regulators. These immunoglobulins ("immunoglobulin inhibitors") arrested estrogen target tumor cell growth completely at low nano-molar concentrations, and their inhibitory effects were entirely reversible by picomolar concentrations of estrogens. That disclosure revealed a previously unknown function for the secretory immune system. In the above-identified patent applications, a major role for TGFβ in breast growth regulation is also identified: it is a cytokine that controls IgA/IgM immunocytes. Breast cancer growth is best defined as negative paracrine control by secretory immunoglobulins (immunoglobulin inhibitors) and positive direct control by estrogens. In conjunction with this work, the longstanding problem of the regulation of estrogen dependent cell growth in culture under serum-free defined medium conditions was solved. These results have great physiological relevance. IgA and IgM are secreted by B immunocytes located in the lamina propria of estrogen target tissues including breast. They are more than 90% of the immunoglobulins secreted into breast milk. The positioning of the immunocytes in the tissue adjacent to the epithelial cells and the secretion of the immunoglobulins is hormone regulated.

In the course of developing suitable serum-free defined culture media for studying estrogen effects on breast cancer cell growth, it was discovered that both soluble iron (FeIII) and diferric transferrin had special roles with regard to estrogen receptor positive ($ER^+$) and $ER^-$ breast cancer cell growth. Even more surprising, the results point to a new estrogen receptor ("ERγ") with a higher affinity for steroid hormone than that of the known receptors ERα and ERβ. In addition, this work led to the identification of a mediating receptor for IgA/IgM that shares the properties of the classical immunoglobulin transcytosis Poly-Ig receptor and is an Fc receptor superfamily member. This receptor maps to a gene location linked to allelic imbalances in 75% of breast cancer specimens. These discoveries lend themselves to major advancements in breast cancer eradication, which are further developed and described herein in a four-part program that has been devised to achieve the goal of eradication of breast cancer. This four-part breast cancer eradication program discloses specific new solutions to the four most pressing aspects of breast cancer eradication:

(1) Local treatment and prevention of spread from a contained breast site (2) Treatment of disseminated (metastatic) breast cancer (3) Reduction in the risk of developing breast cancer (4) Protection against cancer causing agents For the nearly 180,000 women in the United States who will be diagnosed with breast cancer this year, the most important issue is eradication. For some women, eradication means eliminating existing localized disease. Accordingly, in Part I, below, a new non-toxic method for treatment of localized cancers is based on direct application of a soluble form of iron that kills early forms of cancer. Another approach is direct "immuno-therapy" with immunoglobulin inhibitors of cancer cell growth. For other women, eradication means destroying cancer that has moved from the breast to other locations in the body, i.e., disseminated or metastatic breast cancer. Today, even with the best treatments metastatic disease has a poor prognosis. In Part II, below, a number of new therapeutic approaches are presented herein, which exploit cellular nutritional requirements for growth of breast cancer cells. For disseminated breast cancer, a different aspect of iron metabolism is exploited to kill the tumor cells. In addition, the use of a new, previously unrecognized breast cancer gene identified in U.S. patent application Ser. Nos. 09/852,958 and 09/852,547/PCT Published Application Nos. WO 01/86307 and WO 01/85210 as a poly-Ig (Fc) receptor or a poly-Ig-like (Fc) receptor that mediates IgA/IgM inhibition of cancer cell growth is employed in the present eradication program. Until now, the only breast cancer genes known were BRCA1 and BRCA2. The problem has been, however, that BRCA1 and BRCA2 are important for only 1 of 400 women in this country. This leaves 70% or more of breast cancers with no known genetic origin. The new gene shows "allelic imbalances" in 75% of breast cancers. It is a likely candidate for the 70% of breast cancers not explained today. The new breast cancer gene, coding for the poly-Ig (Fc) receptor or poly-Ig-like (Fc) receptor is a potentially valuable candidate for a new gene therapy for disseminated breast cancer because it can restore immune inhibition and anti-estrogen inhibition to a cell and can even lead to cancer cell death.

The surest means of breast cancer eradication is prevention, which is the focus of Part III, below. The Inventor's studies in cell culture have proven that the immunoglobulins IgA and IgM from the secretory immune system can serve to kill early breast cancer cells by terminally arresting their growth. It is now proposed that oral challenge will be successfully employed to reduce the risk of cancer causing mutations in breast cells, as described in more detail in Part IV, below. Immunity is transferred from the gut to the breast via the secretory immune system. This strategy is consistent with the fact that breast cancer incidence is lowest in areas of the world where oral immune challenges are common and highest in the Western countries where similar challenges are restricted. The "hygiene hypothesis" that we are "too clean" will be applied to reduce the current Western world risk of breast cancer (1 in 6-8) to the 1 in 40-100 rate of the non-Western world.

In another view, prevention can mean full eradication worldwide. As proposed in U.S. patent application Ser. No. 09/852,547/PCT Published Application No. WO 01/86307, cancer causing agents are located in the ducts of the breast gland and infectious agents are responsible for the development of breast cancer. It has been known for many years that the majority (i.e. 75%) of breast cancers arise from the cells lining the ducts of the gland. In light of the present disclosure, this is an extraordinary clue to the cause of breast cancer. Microbes and possibly viruses inhabit the milk ducts. Furthermore, there are strong recent clues that cancers may be of microbial origin by virtue of their metabolic products or secreted proteins. The causative organisms will be sought from breast tissue specimens as well as human milk. Conventional-type oral immunizations will be employed to kill the culprit organisms in the ducts. This approach is consistent with other time-tested methodologies, such as Sabin's oral vaccination against the poliomyelitis virus, which is based on the same secretory immune responses that, in the present case, are directed against breast cancer causing bacteria. Alternatively, standard inoculation immunizations with modified microorganisms or fragments of the suspect microbes will be employed to elicit production of natural immunoglobulin inhibitors of cancer cell growth. No matter the general or technical approaches that are ultimately successful, immunizations have been used worldwide to eradicate human diseases. A similar attack is expected to bring an end to breast cancer for a majority of women.

Part I: Local Treatments that Prevent Further Spread from a Contained Breast Site Iron Effects on Local Breast Tumors Methods and compositions for treating localized breast cancer involve iron effects on local breast tumors, and employ nutritional information developed from previous studies of the differential roles of iron metabolism in steroid hormone receptor positive ($ER^+$) and steroid hormone receptor negative ($ER^-$) breast cancer cells. These studies were done with well-known cell lines (29,30,110) grown under serum-free defined conditions (29,30,110) that permitted precise control of free iron (FeIII) and diferric transferrin concentrations (21-30). In U.S. patent application Ser. Nos. 09/852,958 and 09/852,547/PCT Published Application Nos. WO 01/86307 and WO 01/85210 the need to reduce free or soluble Fe(III) concentrations to very low levels to achieve sex steroid hormone or thyroid hormone dependent epithelial cell growth in culture is disclosed, and such disclosure is hereby incorporated herein by reference.

For in vivo treatment of localized breast cancer, preferred forms of iron used and the preferred compositions are described as follows: The most cancer cell toxic forms of soluble Fe(III) presently identified are complexes of ferric ammonium citrate (about 16% iron by weight) and ferric ammonium sulfate. These solid salt mixtures are dissolved in water at high concentrations (1.0-250 mg/ml), and after filter sterilization, and preferably used immediately. These mixtures are light sensitive. Mixtures stored at 4 to 27° C. under normal room light conditions (for example, 3 to 5 days or up to 30 days) show an increase in cytotoxicity of 2 to 10-fold. Higher intensity lights are also effective, using wavelengths ranging from low ultraviolet to visible. Addition of sodium chloride at 0.001 to 0.5 M facilitates the light sensitivity. Addition of up to 0.01 M sodium phosphate, pH 7.0, has a similar toxicity enhancing effect provided it does not cause precipitation. More acidic pH is also effective. More basic pH precipitates the iron complexes. Elevated temperatures to 60° C. increased toxicity. Longer-term storage of up to 30 days increased toxicity in the presence of light or in light shielded containers. It is preferred to use the iron composition immediately after preparation for maximum consistency, particularly when handled under surgical conditions, and to provide a more uniform base for testing efficacy. However, in some situations of use the long shelf-life of the iron compositions is advantageous, and the amount administered can be adjusted for the increased potency of the stored composition. Ferric chloride, ferric nitrate and ferric sulfate were effective, but less so than the iron-ammonium-citrate complexes. This is likely due to greater solubility of the iron-ammonium-citrate complexes. Still other suitable compounds or complexes of ferric iron may exist that also have the desired cancer cell toxicity properties, and it is expected that one or more of those forms of Fe(III) could be substituted for the above-identified forms. In addition to the ferric iron compositions, there are also ferrous iron compositions (e.g., ferrous ammonium citrate) that also kill cancer cells when applied immediately after preparation to a localized breast cancer site, or a mastectomy or lumpectomy site. Preferably the ferrous salt is dissolved fresh and used immediately, as air (oxygen) converts Fe(II) to Fe(III) very quickly. Without wishing to be limited to a particular theory, it is believed that the Fe(II) (ferrous) compounds shower the cancer cells with oxidative products that cause cell death as the Fe(II) is converted to the Fe(III) form. The Fe(III) conversion product then operates to provide further cell killing effects, as described above.

In an in vitro model cell culture system as described in U.S. patent application Ser. Nos. 09/852,958 and 09/852,547/PCT Published Application Nos. WO 01/86307 and WO 01/85210, exposure of $ER^+$ breast cancer cells to sufficient iron causes cell death in $\leq 48$ hours. $ER^-$ breast cancer cells are insensitive to Fe(III) killing under similar in vitro test conditions. These in vitro model systems are believed to be predictive of the in vivo effect of iron treatment on $ER^+$ breast cancer cells.

Another alternative form of iron administration for killing localized cancer cells is prepared by adding $^{59}$Fe(III) to one of the unlabeled (non-isotope) ferric or ferrous salts described above to increase effectiveness. The radioactive and non-radioactive iron can be prepared as the same salt or the admixture of two or more salts of Fe(III). The effectiveness of the composition is increased because any tumor cells not reached by the soluble iron will be exposed to DNA fragmenting $\gamma$ radiation via $^{59}$Fe that penetrates at greater distances.

One other polymeric form of Fe(III) has high inhibitory/toxic activity. The combination of ferric nitrate and bicarbonate is prepared chemically as described (75). After permitting precipitation of ferric hydroxide, and its removal, the polymeric form of ferric-nitrate-hydroxide remains in clear solution indefinitely at room temperature. It is used in this clear solution form.

A pharmaceutical (FDA approved) iron dextran product (INFeD®, Watson Pharmaceuticals, Inc., Los Angeles, Calif.) is available today (137) that has the properties of one suitable preparation for non-radioactive iron treatment of localized breast cancer. It is supplied as a single injection 100 mg dose of iron in 2.0 ml. A series of warnings are supplied concerning the use of INFeD and precautions to be taken with this preparation. There is an indication that animals treated with high doses may develop cancers after repeated injections, however the incidence of such complications in humans is either not clear or very low. However, it is clear that in the older literature sarcomata were found at the injection sites of intramuscular iron (158-160). Evaluation of the literature reveals that sarcomas at the site of iron dextran injection are (i) species specific, with rodents most likely to develop tumors (156), especially after repeated injections (157), (ii) dose and threshold dependent, (iii) residual characteristics at the site, and (iv) latent period relative to the life span of the test species. As reviewed in 1977, introduction of intramuscular iron therapy more than 22 years before then resulted in only nine malignancy reports in man. Of these, only one appears causally related to the iron injections (156). Care must be given to various aspects such as methods of delivery, dilution of drug, and overall iron status of the patients (161). Attention must be given to anaphylactic reactions (161). Current use of intramuscular iron preparations with proper techniques in humans does not appear to bear a significant risk (161). The iron in the preparation associates with serum ferritin or hemosiderin, and to a lesser extent with apotransferrin (i.e. transferrin without bound iron). Care is taken to monitor serum ferritin levels to determine potential iron overload. With intramuscular injection, the majority of the iron dextran is absorbed in 72 hours. The remaining iron dextran is absorbed over the next 3 to 4 weeks. This rate of absorption is compatible with use as a treatment for local breast cancer. For additional cancer cell killing capability, $^{59}$Fe(III) can be incorporated into the iron dextran to increase effectiveness, as discussed above with respect to it use in iron salt solutions.

In still another way in which iron can be used to effect tumor cell death, diferric transferrin is prepared radio-labeled with $^{59}$Fe(III) or $^{55}$Fe(III) (132,133) and is used to irradiate breast cancer cells to cause cell death. Each apotransferrin molecule accepts two Fe(III). These bind at neutral pH with high affinity (i.e. $K_a=10^{20}$) to similar "N" and "C" lobes of the transferrin molecule (136). When breast cancer cells are grown in serum-free cell culture medium containing 0.01 to 20 μg/ml of $^{59}$Fe-transferrin, the radioactive iron from the transferrin becomes incorporated into many cellular components. Subsequent radiation induced DNA damage leads to cell death within 24 to 168 hours. This effect was seen with both ER$^+$ and ER$^-$ breast cancer cells grown in serum-free defined culture medium. Other radio-isotopes such as $^{131}$I-transferrin and $^{125}$I-transferrin (132,133) as well as several other radioisotopes of metals that bind to apotransferrin can be expected to serve an equivalent function. The use of $^{59}$Fe is preferred because of its 44.6-day half-life that is suitable for radiation therapy effectiveness. Yttrium-90 is also a consideration because of its high-energy β emission and 64.1-hour half-life. Of the two iodine isotopes, each has advantages. The $^{125}$I has a longer 60-day half-life compared to $^{131}$I with an 8-day half-life. The $^{131}$I has higher energy. The advantages of the different isotopes in killing of ER$^+$ and ER$^-$ breast cancer cells will be evaluated first in cell culture and then using in vivo rat mammary tumor induction models as described herein.

Another alternative method and composition employs an insoluble form of radio-labeled iron, which is prepared by methods previously described (27). When it is necessary or desirable to limit the amount of radiation to a restricted site, such as with mastectomy or lumpectomy, or to a specific set of axillary nodes, the $^{59}$Fe can be delivered via a complex of deferoxamine-Sepharose. Deferoxamine is covalently attached to Sepharose (27), or to any other "activated" insoluble matrix (human compatible) by the methods described or derivative methods. Deferoxamine is a low molecular weight bacterial product that is currently in use as DESFERAL® (Novartis Pharmaceuticals Corp., East Hanover, N.J.) to treat human iron overload patients (138). Deferoxamine binds Fe(III) with a very high affinity (i.e. $10^{23}$). The complex of deferoxamine-Fe(III) does not dissociate under body conditions. Thus, placement of insoluble deferoxamine bound $^{59}$Fe in any site will effectively expose a local area to high-energy γ radiation with escape of only minimal labeled Fe(III).

It may be preferable to select a biodegradable matrix (e.g. dextran, starch or insoluble protein or biodegradable polymer) in some cases or a stable/non-degradable matrix (e.g. cellulose or synthetic biomatrix) in others. Another application includes attachment of the deferoxamine to non-degradable "biobeads" for implantation directly into the local tissue for specific periods of time. The visible non-immunogenic beads can be removed at times deemed desirable or when the desired effect has been achieved, or they can be removed at the time of mastectomy or lumpectomy.

Localized Breast Cancer Eradication. In earlier studies of the role of nutrients, hormones and growth factors in hormone responsive pituitary tumor cell growth in serum-free chemically defined culture, it was observed that 1 μM soluble iron in the form of Fe(III) inhibited growth (21-28). Exposure to 10 μM Fe(III) killed these cells. The results were thought initially to be applicable only to rat pituitary cells. However, they have proven useful with ER$^+$ breast cancer cells (29,30). To develop in vivo confirmation that iron can be used to locally treat breast tumors, a series of experimental animal models will be investigated.

The use of iron for the treatment of cancer is a clear departure from the widely held belief or paradigm that Fe(III) cannot be (or should not be) administered locally in vivo. It is commonly cited (87) that Fe(III) released from cellular ferritin induces (•OH) free radical formation and that this reactive species modifies proteins, lipids and nucleic acids (120). Thus, investigators generally view iron as cancer initiator or promotor (87,121-125). That paradigm is not pertinent to the present therapeutic forms of Fe(III), however, because in the present case the metal will act only short term. The Fe(III) applied to the tumors is extracellular and has little or nothing to do with the complex models developed for explaining the putative role of intracellular ferritin H chain in oxidative damage to cells (120,121). Notably, as is indicated (121), much of the ferritin oxidative model is presumptive and unsubstantiated. Furthermore, ER$^+$ breast cancer cells appear to be exquisitely sensitive to a putative burst of extracellular oxidative products. These cells die very quickly when non-protein bound Fe(III) is added to culture medium. It should be noted that free Fe(III) does not support epithelial growth. Diferric transferrin is required. For cancer treatment, the period of exposure in vivo will be limited by the fact that within a few days the Fe(III) will be converted to the inactive but metabolically useful forms of monoferric and diferric transferring and ferritin. Free/soluble Fe(III) is expected to bind to apoferritin and apotransferrin under physiologic conditions. Plasma contains about 2 mg/ml of apotransferrin and 1 mg/ml diferric transferrin (i.e. transferrin is 66% unsaturated with iron in plasma). Since Fe(III) cell killing happens in less than a few days, the risk of other adverse effects of the iron are minimized. Certainly long-term mutagenic effects are minimized. The time of exposure and dose schedule of free Fe(III) will be kept to the minimum needed to achieve therapeutic results. This is the same principal used with short doses of γ radiation and short-term applications of chemotherapy used today to treat breast cancer. In fact, the very same argument can be made against the radiation protocols used today to treat localized breast cancer, which run contrary to the paradigm that excess radiation can induce tumors. Likewise, several of the current chemotherapy chemicals are actually mutagenic. Therefore, they are used in regimens that kill tumor cells but stop short of causing a substantial increase in other cancers.

Further support for the value of this approach comes from the Physician's Desk Reference information (137) discussed above, in which humans are treated with intramuscular injections of iron dextran (INFeD) to correct iron deficiencies that are not treatable by oral therapy. While there have been individual reports of the appearance of sarcoma tumors at the injection site in humans (137), such reports could not be confirmed by the manufacturer at the present time (personal communication with Watson Pharmaceuticals, Inc.). The frequency of such tumors as a proportion of the total injections per year or patients treated per year is not available, but is presumed to be very low.

The use of systemic iron or orally administered iron causes an increase in the body content of this metal and in plasma ferritin and diferric transferrin levels. One report states that increased dietary iron facilitates carcinogen induction of rat mammary tumors and estrogen induction of Syrian hamster kidney tumors (139). Another report (140) states that excess iron again appeared to facilitate carcinogen induced rat mammary tumors, but there was more care given to control the effects of various iron status states on body weight gain and hematocrit. The effects of excess iron were only apparent later in that study. In another study, support for a critical role of iron was not found with the rat mammary tumor models (141). In the present case, it is concluded that increased saturation of apotransferrin by dietary iron results in greater growth rates in carcinogen induced rat mammary tumor cells. This is consistent with a previous showing with a carcinogen induced rat mammary tumor cell model in culture that diferric transferrin is absolutely required for growth (142,143). Apparently, the systemic elevation of plasma iron is conducive to growth of breast cancer cells. Any therapy with Fe(III) for treatment of breast cancer is therefore, preferably local and is subject to natural elimination within a period of a month. Preferably the doses are managed such that they do not substantially elevate plasma ferritin or the iron saturation percent of transferrin.

Today, women with localized breast cancer have two initial surgical options: mastectomy or breast conserving surgery as known as "lumpectomy". With increasing frequency, pretreatment is done to shrink primary or nodal tumors before surgery. According to the present plan, an animal model will be used to test whether iron in the form of soluble ferric ammonium complexes can destroy existing tumors, or can eliminate undetected cells within mastectomy/lumpectomy sites. Initially, this program will include testing the direct effect of Fe(III) on estrogen growth responsive tumors developed from rat mammary MTW9/PL2 cells in W/Fu female rats (34,35). Studies will test treatment by application directly into tumors or into their immediate blood supply. Additionally, after tumors have developed they will be resected and the surgical site treated with soluble Fe(III) to determine effect on recurrence. It is known that without any treatment, there is a 40 to 60% recurrence rate in four months in rats.

With a different model based on CD-rats, environmental carcinogens will be used to induce rat mammary primary tumors as described (36) before initiating localized Fe(III) treatment. The primary carcinogen induced rat model selected has many characteristics of human breast cancer (37) and therefore is considered relevant.

Another model also has special relevance. It is now clearly established and almost universally accepted that estrogens promote target tissue cell growth (109). There is still a question about the exact DNA and functional sequence of the receptor that mediates this response (29,30). However, these steroids may have a second function. Investigators have long proposed that estrogens (or their metabolites) are genotoxic and cause mutations (107,108). Estrogens are considered central to human female breast cancer development even beyond their growth promoting function. There is a rat mammary tumor model that mimics this dual effect. Estrogen (17β-estradiol) treatment of female ACI rats induces mammary tumors in 100% of the population within 197 days (49). The tumors are estrogen growth responsive. This model will also be used to induce tumors and determine the effects of iron therapy on the primary neoplasms. Positive results with this model will have special applicability to human cancers. Local treatment with Fe(III) provides an entirely new first line of eradication of breast cancer.

In parallel studies, the animal tumor models described above will be injected or otherwise treated with the $^{59}$Fe-deferoxamine-Sepharose complex and the effects on tumor mass monitored. This same procedure will be assessed for its effect on recurrence of resected tumors. This is believed to be a completely new approach to local breast cancer eradication. The effects of soluble Fe(III) versus those of immobilized $^{59}$Fe will be compared for tumor regression, survival of the hosts and effects of both treatments on the physiological health of the animals. Confirmation obtained in these in vivo rodent studies will indicate the applicability of, and will supply partial evidence for FDA approval for, human trials. Today, the only other direct local breast cancer treatment without systemic effects is radiation, which causes healing problems post-surgery and other chest wall and organ complications.

Part II: Treatment of Disseminated (Metastatic) Breast Cancer

Methods of Treating Disseminated Breast Cancer

The problem of eliminating disseminated or metastatic breast cancer is profoundly different than eradication of primary localized breast disease. These forms of breast cancer are most often chemotherapy resistant and nearly always fatal. Today there is no satisfactory chemotherapy or any other therapy for these cancers. In a marked departure from conventional theories and methodologies, effective treatments for both $ER^+$ and $ER^-$ disseminated breast cancers have been devised.

Iron Metabolism and Disseminated Breast Cancer. It has been found that diferric transferrin is unconditionally required for both $ER^+$ and $ER^-$ human breast cancer cell growth. It is clear that ER$^+$ cells are under both hormone and growth factor control. However, ER$^-$ cancer cells no longer require growth factors or hormones for proliferation (29,30). Only nutrients are required. It is a common observation that hormone autonomous breast cancer cells have also escaped the requirement for exogenous growth factors. However, without an adequate supply of iron delivered by transferrin, both ER$^+$ and ER$^-$ breast cancer cells fail to survive. Iron is required for DNA synthesis and other key metabolic processes (38). Of the known types of chelators, the present studies indicate that only those that remove iron from diferric transferrin and serum ferritin will be useful for iron deprivation in tumors. An example of a class of chelators that are able to successfully withdraw iron from serum ferritin and diferric transferrin are the α-ketohydroxypyridine chelators (144). Other classes are also known, and some of these may also be suitable for use as described herein for combined treatment modalities. Deferoxamine does not remove iron that is already bound to transferrin.

A second or alternative approach is to use monoclonal antibodies against the transferrin receptor to prevent iron uptake. This has yet to be developed into an effective treatment (42-44). Monoclonal antibody therapies alone are often ineffective because (i) there is a large supply of the competing natural ligand available that competes with the antibody for receptor binding, (ii) the natural ligands often have higher affinity for the receptor than the blocking monoclonal antibody, (iii) antibodies often do not escape the blood readily, and (iv) humanized antibodies are required for repeated/prolonged treatments.

Another approach that can be employed as part of the breast cancer eradication program is to block transferrin directly in the plasma so that it will not be a source of iron for cancer cells. Current results support the view that diferric transferrin can bind to cellular transferrin receptors via either the "N" or "C" lobes (118) or that binding is primarily via the "C" lobe (119). Because the lobes have similar amino acid sequences, it is likely that the same receptor recognition sequence is present in both. Most notably however, the amino acid sequence of diferric transferrin that codes for receptor binding is not known. This sequence will be identified using techniques that are well known in the art (e.g. by phage display technology) and specific monoclonal antibodies will be raised to block transferrin binding to cellular receptors, employing standard techniques. This will prevent the use of serum-borne diferric transferrin by cancer cells and thus starve cancer cells for iron. This approach does not suffer from several of the problems of receptor binding monoclonal antibodies just cited above. The anti-receptor recognition monoclonal antibody is not required to leave the general circulation to be effective.

Iron Chelation Depletion and Combined Modalities. To deplete iron from the diet, deferoxamine can be given intravenously or other chelators used orally. This will further lower the blood plasma content of diferric transferrin and increase the effectiveness of the receptor sequence monoclonal antibody just described above. This treatment should be combined with a low iron diet. In addition, many other oral drugs are available to reduce the effective body load of iron. These can be used in combination therapies to deprive the cancer cells of necessary iron sources.

Genetically and Chemically Modified Transferrin. In addition, genetically and chemically modified transferrin can be used to introduce lethal doses of specific toxins and cytolytic enzymes that kill cancer cells. For example, RNAse can be genetically engineered or chemically attached to transferrin, using techniques that are well known in the art. Delivery of this cytotoxic enzyme via the transferrin receptor can be expected to cause cell death. Most importantly for this disclosure, the most dangerous (i.e. rapidly growing and spreading) ER$^-$ breast cancers over-express the transferrin receptor (129). Genetically modified transferrin will be developed that is cytotoxic and/or unable to act as iron donor to cells. This strategy focusing directly on transferrin has the advantage of acting systemically without regard to the issue of tissue penetration by receptor blocking monoclonal antibodies or the necessity of developing "humanized" monoclonal antibodies. In some instances it will be preferred to combine modalities that interfere with iron metabolism in order to achieve the most satisfactory and effective results. The above-described rat mammary tumor models will be employed to confirm the suitability of this treatment modality for human trials.

Immunotherapy of ER$^+$ Breast Cancer. As discussed above, studies in cell culture with ER$^+$ breast cancer cells have shown that contact with IgA and IgM causes cell death within three weeks (29,30). These results will be employed in immunotherapy for breast cancer based on the smaller, more tissue penetrating, Fc domains of polymeric IgA and IgM. The use of Fc fragments is planned because of data indicating their importance in causing cell growth inhibition. The rat mammary tumor models described above will be used to continue testing in vivo.

The natural forms of IgA and IgM, as well as the Fe fragments, can be administered intravenously. Several immunoglobulins including IgA and IgM are already FDA approved for human use. Those preparations, as well as other secretory immunoglobulin preparations, are expected to be useful for inhibiting cancer cell growth when administered in various pharmacologic amounts. A suitable pharmaceutical composition must provide IgA and/or IgM in a form that is capable of producing the above-described inhibitory effect on estrogen dependent breast cancer cell growth, and the immunoglobulin component must be able to bind to the poly-Ig (Fe) receptor or poly-Ig-like (Fe) receptor that mediates such inhibition. The preferred active compositions (i.e., cell growth inhibitory) contain dimeric/polymeric IgA and pentameric IgM and an activity-stabilizing medium (e.g., a steroid hormone stripped non-heat inactivated serum or purified compositions containing calcium), as described in U.S. patent application Ser. Nos. 09/852,958 and 09/852,547 (PCT Published Application Nos. WO 01/86307 and WO 01/85210), incorporated herein by reference. To treat localized breast cancer, oral immunization challenge will also be used to increase the number and function of IgA and IgM secreting B immunocytes in the breast tissue and thereby provide more inhibitory/ killing immunoglobulins. This treatment has the advantage of not requiring a clinical setting for administration and being applicable to all women regardless of age or physical condition. This immunotherapy can be combined with tamoxifen anti-estrogen or combined with other immune modulating drugs that increase the function of the secretory immune system in the breast. Preventative and risk reduction methods and compositions are described in co-pending U.S. patent application Ser. No. 10/293,439 entitled "Anti-estrogen and Immune Modulator Combinations for Treating Breast Cancer," the disclosure of which is incorporated herein by reference. This treatment mode may have special application to breast cancer in situ, a form of the disease that has not left the ducts and often recurs in the same breast after lumpectomy or in the other breast.

Gene Therapy and Anti-estrogen Therapy Combined for ER$^+$ Breast Cancer. A new function for the well-known anti-estrogen tamoxifen has been discovered (29,30). Tamoxifen mimics the estrogen reversible inhibitory properties of immunoglobulins IgA and IgM to inhibit ER$^+$ breast cancer cell growth. Tamoxifen acts in the complete absence of estrogens. This indicates a function unrelated to its classical interaction with the ER$^-$ (79). In related studies (29,30) it has been recognized that the cell surface receptor mediating the growth inhibitory effects of IgA and IgM is a member of the imnuunoglobulin superfamily of receptors and shares the properties of the poly-Ig receptor and Fc family receptors. The receptor properties have been described and discussed (29, 30). Data indicate that tamoxifen only inhibits the growth of cells containing this immunoglobulin receptor. Furthermore, the immunoglobulin mediating receptor appears to be under the control of either sex steroid hormones or thyroid hormones. Hence, loss of the sex steroid hormone receptor (or the appropriate thyroid hormone receptor from among several thyroid hormone receptors) causes an equal loss of the superfamily receptor. This information can be combined to develop a new, more effective gene therapy for breast cancer. ER$^-$ cells lacking the superfamily receptor can be restored to immunoglobulin control by infection with an immunoglobulin binding receptor DNA bearing virus vector, using conventional DNA transfection techniques. As a result, tamoxifen will then become effective even with the transfected ER– breast cancer cells, and can be used to kill these cancers as is done today with ER$^+$ cancers. This is an entirely new combination of gene therapy and anti-estrogen therapy.

Gene Therapy and Immunotherapy Combined for ER$^-$ Breast Cancer. Another approach to eradication of ER$^-$ disseminated breast cancer has been devised. Gene therapy can be targeted to human breast cancers via the over-expressed transferrin receptor. Gene therapy using the poly-Ig-like Fc receptor will be used to reestablish immune negative control of autonomous breast cancers that would otherwise grow uncontrolled. In related studies (29,30) it has been established that exposure of breast cancer cells bearing this receptor to IgA or IgM leads to cell death by arresting cancer cell growth. By developing gene therapy and coupling it with either oral "immunization" to boost systemic immunoglobulins or direct intravenous use of suitable human immunoglobulins, new treatments for disseminated breast cancer can be established. The rat mammary tumor models described above will also be used to establish the first applications in vivo. Use of athymic nude mice and human breast cancer xenografts will be used to establish human relevance.

Disseminated or Metastatic Breast Cancer Eradication using Radioactive $^{59}$Fe. The radioisotope $^{59}$Fe is a high-energy γ emitter that disrupts breast cancer cells in culture by fragmenting DNA. This proposal plans the use of transferrin as a $^{59}$Fe delivery system to both disseminated ER$^+$ and ER$^-$ breast cancers. Because these cancers have such a high requirement for iron bound to transferrin, the delivery system may only need low concentrations of this high-energy isotope. Rat mammary tumor models are available to investigate this therapy, as described above. It is expected to be effective because growing cells concentrate more iron than static normal cells. This modality may be especially effective with blood replacement therapy, described as follows.

Blood Replacement Therapy and Cancer Eradication. A number of companies are now well advanced in the development of "artificial blood". The FDA expects that within a year or two a blood substitute will become available. Many treatments, such as gene therapy and the above-described iron therapies may be enhanced. Others such as standard adjuvant chemotherapy are expected to be more selective and effective in substitute blood where the levels of interfering substances can be regulated. This approach may also increase the effectiveness of tamoxifen and the newer "pure" antiestrogens. Since each treatment round is expected to last only a few weeks to a month, a substitute blood product may be employed in one of the above-described therapies, as part of the present breast cancer eradication program.

This approach may have special application to the treatment of disseminated breast and other cancers because artificial blood can be prepared free of diferric transferrin, which is usually present in physiological human blood at about 1.0 gram per Liter. Addition of low concentrations of radio-labeled diferric transferrin to artificial blood will avoid the dilution caused by the natural blood diferric transferrin and therefore increase the effective dose of radioisotope to cancer cells without exposing the body to high levels of radiation.

Part III: Reduction of Risk of Developing Breast Cancer

Overview. The risk of developing breast cancer for women in the United States has been rising steadily for the past several decades. It will soon approach one in eight. It is fortunate that new treatments and more effective screening methods have kept mortality rates from rising dramatically. Nonetheless, more than one hundred women are lost per day to breast cancer in the United States. Researchers and health care providers understand that the first line of defense against this disease is prevention. If the long term outlook for all women is to be improved, and especially if our daughters to be free of this threat, the focus must now be on finding a prevention.

As described above, a recent breakthrough in understanding how breast cancer grows reveals that, in its initial stages, breast cancer cells are inhibited and even killed by the secretory immune system (29,30). That means a part of our immune system can stop early cancer cells from growing. During adult life, breasts produce milk or milk-like fluids. These fluids contain high concentrations of three immunoglobulins, IgA, IgM and IgG1. These are passed from mother to child during breast-feeding, and protect the child from bacterial infections. As a result of this discovery, and considering the fact that long duration breast-feeding is known to reduce the risk of breast cancer, it is proposed that these immunoglobulins are likely to protect the mother against breast cancer via this newly discovered inhibitory mechanism. This presents an unexpected opportunity to rethink the problem of prevention and to apply new, unconventional approaches.

The present plans for a new type of oral immunization for breast cancer were advanced by another remarkable fact about the secretory immune system. The immunocytes of this system permit mothers to protect their suckling offspring from infectious pathogens. Because both mother and young child are exposed to the same infectious agents at the same time, but only the mother can develop immunity (or already has it), how does the young offspring fight off disease? The answer is that infectious agents orally entering the mother's body cause an antibody response in areas of the intestinal mucosa called Peyer's patches. These lymphoid structures cause the production of B immunocytes that ultimately populate breast tissue. Once there, the B cells secrete milk-borne immunoglobulins with specificity against the offending infectious agents.

It is proposed that oral "immunization" is expected to be most effective during a first susceptibility age range "window" (e.g., during puberty, or 9 and 19 years of age), and/or during a second "window," after menopause, when secretory immune system function decreases sharply. If the secretory immune system of the breast is stimulated at times when women are known to be most susceptible to breast cancer, it might be prevented or at least the risk of occurrence considerably reduced.

Finally, recent developments in mucosal cancers other than breast cancer suggest another application of this discovery. As discussed above, it is now understood that at least one mucosal cancer is of bacterial origin. The bacterium *Helicobacter pylori* is a Class I carcinogen thought to cause gastric cancer. This fact, coupled with the discovery of new secretory immune functions in the breast, supports the proposal that breast cancer might arise from an infectious agent. Plainly, there is no known cause for 70% or possibly more of breast cancers, although environmental carcinogens are most often named as culprits. Nonetheless, bacterial participation or a bacterial origin remains entirely possible. If such was proven, the development of pathogen specific breast immunity via oral challenge would offer a unique approach to immunization.

In the history of cancer research, oral immunization has been investigated mostly from the point of view of treatment. However, there has been no serious application to either the treatment or prevention of breast cancer, which is surprising since oral immunization is so readily adaptable to mass populations of women of all ages and all circumstances. Applying oral immunization as a new means of preventing breast cancer is a preferred part of the breast cancer total eradication program.

Oral Immunization to Reduce the Risk of Breast Cancer

During adult life, breasts produce milk or milk-like fluids that contain high levels of three immunoglobulins, IgA, IgM and IgG1. In cell culture these immunoglobulins not only block early breast cancer cell growth, but if elevated for a period of time, will kill breast cancer cells. This discovery presents the unexpected opportunity for a new oral immunization for breast cancer, taking advantage of a basic function of the secretory immune system: the natural production of IgA and IgM.

It is proposed that oral immunization be administered when it might be most effective, i.e., during the same susceptibility age ranges that were identified in data collected from survivors of the atomic bomb blasts during World War II, which showed an unexpected pattern of breast cancer development. Those exposed to the radiation between 9 and 19 years of age developed breast cancer at much higher rates than survivors who were 30 years or older (45). This meant there was a "window" early in life when breast tissue was highly susceptible to DNA modifying mutations. This same pattern became clear again when women survivors of Hodgkin's disease were studied. Treatment of Hodgkin's requires agents that cause DNA damage. Women treated between 11 and 19 develop breast cancer at higher rates than women whose treatment began at later ages (46). Again, young women appeared to have a "window" of susceptibility. This same "window" is well known in experimental animals exposed to carcinogens (47,48).

Young women might not be alone in experiencing increased susceptibility, however, as secretory immune system function decreases sharply after menopause. This coincides with the time when breast cancer rates achieve near their highest levels (145), and may represent a second "window" not previously recognized. If the secretory immune system of the breast is stimulated at times when women are known to be most susceptible to breast cancer, it might be prevented or at least the risk of occurrence considerably reduced.

Rat mammary tumor models are being used to define the conditions for increasing breast tissue IgA/IgM secreting immunocytes and determining if this protects against the DNA synthesis dependent damage effects of estrogens as carcinogens (49) as well as the effects of environmental carcinogens (36). Conditions and appropriate oral bacterial challenges (i.e. non-pathogenic and pathogenic *E. coli*) to increase breast cell B immunocytes and therefore increased secretion of IgA/IgM are being defined. It is known that women from the non-Western world have high levels of antibodies to fecal *E. coli* in their milk. An example study compares women from the United Kingdom and Sri Lanka (146, 148). These women also have the lowest risks of any worldwide. In the present disclosure, it is now proposed that these microorganisms, live or attenuated, or fragments or molecules from them, will be potential agents for inducing breast cancer immunity (153). Oral immunization is not the only administration route to be considered. Nasal, rectal and vaginal administration must also be considered (150,154). Antigen challenge may be required on a routine schedule since oral immunity may not be permanent. Multiple challenges are most likely necessary to maintain full immunity. This means placing the challenge in a delivery form suitable to the site of challenge. For orally administered treatments a tablet, a food product, a food drink, or the like may be most useful and readily accepted by women. When increased secretory immune function has been established, the effect of the immunoglobulin cell-growth inhibitors on attenuation of pre-malignant changes in breast ductal cells will be evaluated as described (56-58).

Another route for presenting the bacterial antigens to women of all ages on a routine schedule is in genetically engineered food. Potatoes, tomatoes and bananas can be genetically engineered to express foreign antigens such as those from a virus or bacteria (151,152). Oral immunity expressed by mucosal tissues can then be achieved on a routine basis by consumption of the genetically developed food product (151-155). This route for administration has worldwide applications. This technology has not been previously applied to immunization of breast, prostate, colon, kidney, ovary or endometrial cancer.

Part IV: Eradication by Conventional Immunization Against the Infectious Agents that Cause Breast Cancer Infectious Origin of Breast Cancer and Mass Immunization A bacterial origin of cancer is a growing theme, however this has not always been the case. The work of Marshall & Warren in 1982-1984 was a milestone, in which their identification of a genus *Campylobacter* organism in gastric ulcers from biopsy specimens changed our thinking completely. Notably, *H. pylori* was unheard of 20 years ago. The notion that gastric ulcers were caused by a bacterium was unprecedented. Initially, the skeptical scientific community rejected this idea. Today it is a recognized etiology of a major human disease (15).

Finding a clue to the origin of breast cancer comes from the fact that 75% of breast cancer is invasive ductal carcinoma, it is now proposed that the agent causing ductal carcinoma exists in the ducts. As with all mucosal tissues, breast ducts are open to the exterior; it is likely that infectious agents enter the ducts. The question is can these organisms cause breast cancer?

Today it is recognized that bacteria are long-term participants in cancer development (14,18,19,103) including gastric (15,16), colon (50,51), cervical (17), and very likely prostate (104) cancer. The concept that bacteria are involved in colon cancer is more applicable to breast cancer than the *H. pylori* model. Investigators studying the colon model offer some important insights. The bacteria involved in colon cancer are not obvious at histologic examination and do not cause ulcers or severe inflammation as does *H. pylori*. Instead, *Bacteroides* in colon produce fecapentaenes that are potent mitogens (i.e. they cause cells to grow and divide) (51). By way of comparison, breast atypical hyperplasia (i.e. increased growth rates above normal) is known to be a pre-cancerous condition that also does not show severe ulceration or major inflammation. It is expected that breast bacteria also cause DNA synthesis and cell growth necessary to make cancer-causing mutations permanent.

Human milk contains many microorganisms (52-55). They are believed to be skin and nipple contamination of expressed breast milk. Then again, in some samples, the organisms were not usual skin flora (52). In one larger study, several pathogenic organisms were found along with non-pathogens (53). No virus particles were identified in the milk. The fact that bacteria are present on the nipple and surrounding skin certainly leaves open the possibility that they might migrate into the ducts. To date, no microbes have been investigated from the perspective of causative agents of breast cancer.

Data supporting the likely presence of at least low levels of bacteria in ducts comes from two different sources. First, human milk lipids have been modified by chemical reactions to generate genotoxic agents (56-58). The presence of these agents is measured directly by DNA damage of breast cells obtained from milk. Because genotoxic components are in freshly expressed milk, the products are thought to be endogenous to the breast. In another study, samples of freshly expressed human milk contained N-nitroso-dimethylamine, nitrate and nitrate reducing microorganisms (59). This study concluded that the compounds arose endogenously. These reactive nitrogen compounds are likely cancer causing agents in other tissues. It is highly probable that reactive lipids and nitrogen compounds are formed endogenously in human milk ducts.

Considering that the development of breast cancer is a multi-step process that often leads to tumor cell heterogeneity (111), it is now proposed that the steps leading from normal duct epithelium to hyperplasia to pre-malignant changes and finally to in situ carcinoma and invasive ductal carcinoma (112) are caused by a relatively continuous source of mutagenic agents that are present over a number of years. Furthermore, because each change at each step requires DNA replication in order to become permanent, it is likely that both estrogens and the causative bacteria induce cell proliferation. Since bacterially induced mammalian cell proliferation related to cancer development is known, the proposed model for bacterial causation takes into account the very well known (112) progression of normal breast epithelium as it transitions to invasive ductal carcinoma (i.e. the form in 75% of breast cancers).

In further studies, human milk, breast cancer samples and normal breast tissue (reduction mammoplasty) will be examined for bacterial content. They will be analyzed for bacterial content by culture (aerobic and anaerobic) and PCR methods (62-65). Example techniques to be applied include (i) use of specific PCR primers for known and new bacteria, (ii) PCR amplification of conserved 16S rRNA sequences, and (iii) RDA-PCR which is also called "reverse PCR". These can be used to identify unique infectious agents in tissues, even in paraffin embedded specimens (61). PCR technology pertinent to the identification of most microbes that this study might encounter is now being applied.

Next, colony-derived bacteria will be used in the "Ames test" to identify mutagen production (66). Culture medium from the bacteria isolated can be tested directly for mutagenic activity using any of several strains of *Salmonella*. Candidate organisms can be grown plus and minus human milk components to determine the source of the mutagenic agents. The different types of existing screening methods have been reviewed (67). Improvements in the Ames test have been introduced to provide more quantitative evidence that the assay is providing significant results with respect to cancer bioassays (68,69). The results of this test will establish which bacterial isolates produce mutagenic metabolites. The Ames test can also be applied to demonstrate that the bacteria cause an "oxidative burst" mediated by neurophils and macrophages. In this case, the leukocytes are incubated with the bacteria to generate the active mutagenic species. This approach resolves the issue of whether the products of the bacteria are the mutagens themselves or if the activation of leukocytes is required.

Bacteria that meet the criteria described above will be cultured and the medium tested with non-tumorigenic human breast epithelial cells (Clonetics, San Diego, Calif.) or epithelial cells derived from human milk (56,58) for transformation activity. The human milk derived HBL-100 non-tumorigenic cells are also candidates for this assay. The cells will be tested for colony formation in soft agar. Tumor or transformed cells will form colonies. There is a strong correlation between colony formation in soft agar and tumorigenicity in animals. This approach will confirm that the Ames test translates to transformation of human breast cancer cells. Candidate cell lines will be analyzed for tumor formation in athymic nude mice.

In addition to the above analyses, the bacterial isolates are expected to have an additional immunoprotective mechanism. Breast secretions contain high concentrations of secretory IgA that kill bacteria by the known antigen-antibody recognition function. This is a first line of protection against breast duct infections by many strains of bacteria. However, some bacteria can escape IgA killing by secreting proteases that cleave the IgA into inactive Fab and Fc fragments.

In a final test, an animal model will be sought to determine if infection leads to breast cancer development. Several strains of inbred and outbred rats are highly susceptible to breast cancer induction. Candidate bacteria will be introduced into the breast by milk pump (60) and tumorigenesis monitored.

The final step will be to use the attenuated organism, or entities derived from the organism, to test for oral induced immunity in human breast milk as has been described (148, 149). Once immunity against the mutagenic bacteria is established in human milk, studies can move forward to determine if this method reduces the risk of developing breast cancer.

Surrogate end points will be used to estimate the effectiveness of oral route administration of immunogen. Because a full clinical trial of an oral immunization may require five or more years to establish efficacy, DNA changes in cells isolated from milk or breast fluids of women being administered the treatment will be studied. By using this surrogate end point approach, a reduction in genotoxic (i.e. mutagenic) events can be identified within months. This will provide data to support more expensive long-term clinical studies.

The same antigen preparation protocols can be used with direct immunizations by standard methods such as intramuscular injection. Many approaches to standard immunizations are known and commonly employed in worldwide programs to eradicate infectious diseases. The oral route of immunization utilizing the secretory immune system is considered preferable because the antibody is delivered directly into the intraductal space where the causative bacteria are then neutralized.

CONCLUSIONS

The program and procedures described above advance directly to the core problem of eradication of breast cancer. Today there are women battling breast cancer and others already developing the pre-malignant changes leading to the disease. For them eradication means availability of effective treatments, especially for chemotherapy resistant metastatic cancer. Treatment will likely remain an important issue for several years to come, and must therefore be given serious continuing consideration. Very definitely, this means developing new methods of eradicating metastatic breast cancer. One aspect of the present eradication program departs from the usual chemotherapy regimens to exploit the nutritional requirements for growth of breast cancer. Cancer cells grown in culture invariably require iron in the form of diferric transferrin for growth. With the advent of the very powerful tool of serum-free defined cell culture (113-118), this requirement could be established conclusively (29,30,113-117,135). Variations in this requirement usually result from differences in the level of storage of iron as ferritin (126) in the cells. When ferritin stores are depleted, iron must be acquired from the outside of the cells via the specific iron carrier transferrin (136) and internalization via specific cell surface transferrin receptors (127,128,134). The same logic/hypothesis employed in the breast cancer eradication program is extendable to all epithelial cancers (80% of the total cancers in humans) and for lymphoid origin cancers, sarcomas (i.e. cancer of the connective tissues and muscle) and cancers of the bone and nervous system. Indeed, it is absolutely clear that iron is required for the growth of all cells because of its involvement in metabolic processes and DNA synthesis (124, 130,131). It can be readily appreciated that the disclosed concepts and procedures involving the exploitation and/or interruption of iron metabolism required for cancer cell growth apply to many if not most cancers of humans.

The eradication of breast cancer will likely come from a different direction than the common themes of genes and cell signaling pursued by so many investigators today. The work leading to the new eradication program comes from the discovery of the role of the secretory immune system in estrogen responsive breast cancer cell growth, described in the two U.S. patent applications cited above. Based on this discovery, the plan for an "oral immunization" to protect breast cells from DNA synthesis dependent mutagenic events has been devised. The goal is to reduce risk from the current 1 in 8 to a level of 1 in 40 or 50. This plan is consistent with the growing, but still widely ignored, concept that the population of the Western world is placed at higher risk for mucosal cancers because we are "too clean." Our immune systems are not challenged sufficiently to protect us.

An additional immune based eradication plan finds support in an unexpected source. It is known that bacterium *Helicobacter pylori* is the most common cause of gastric ulcers. It also is the first bacterium to be a definite cause (Class I) of a human cancer as rated by the International Agency for Cancer Research (14,15). A number of infectious agents have been documented to cause or contribute to human cancers (14-19). However, this information has had little or no impact on the search for the origin of breast cancer. More commonly, it has been proposed that environmental chemicals cause the possible majority of human cancers. Indeed, despite advances in defining various breast cancer risks due to chemical exposure (20), the perplexing element of randomness without clear indications of chemical exposure has not been explained. An infectious origin is random, and therefore a reasonable alternative. Breast cancer risk is sometimes familial but most often is not genetic (i.e. inherited) for most women. Indeed, this is a characteristic of the incidence pattern of ulcers in *H. pylori* infected families (16). While not all infected cohabitants develop gastric ulcers or gastric cancer, members of a family tend to have higher incidences than average. By seeking infectious agents as either the cause or as major contributors to breast cancer development, and then using that information to develop appropriate immunizations, it is expected that the incidence of breast cancer will be reduced or eliminated.

REFERENCES (1) Barnes D & Sato G (1980) Growth of a human mammary tumor cell line in serum-free medium. Nature 281;388-389.
(2) Goustin A S, Leof E B, Shipley G D & Moses H L (1986) Growth factors and cancer. Cancer Res 46:1015-1029.
(3) Jensen E V & Jacobson H I (1962) Basic guides to the mechanism of estrogen action. Recent Prog Horm Res 18:387-414.
(4) Jensen E V & DeSombre E R (1973) Estrogen-receptor interaction. Estrogenic hormones effect transformation of specific receptor proteins to a biochemically functional form. Science 182:126-134.
(5) O'Malley B W & Means A R (1974) Female steroid hormones and target cell nuclei. Science 183:610-620.
(6) Sirbasku D A (1978) Estrogen-induction of growth factors specific for hormone-responsive mammary, pituitary, and kidney tumor cells. Proc Natl Acad Sci USA 75:3786-3790.
(7) Sonnenschein C & Soto A M (1980) But . . . are estrogens per se growth promoting hormones? J Natl Cancer Inst 64:211-215.
(8) Lykkesfeldt A E & Briand P (1986) Indirect mechanism of oestradiol stimulation of cell proliferation of human breast cancer cell lines. Br J Cancer 53:29-35.
(9) Sirbasku D A (1981) New Concepts in control of estrogen-responsive tumor growth. Banbury Report 8:425-443.
(10) Ikeda T, Liu Q-F, Danielpour D, Officer J B, Iio M, Leland F E & Sirbasku D A (1982) Identification of estrogen-inducible growth factors (estromedins) for rat and human mammary tumor cells in culture. In Vitro 18:961-979.
(11) Sager R (1998) Expression genetics in cancer: shifting the focus from DNA to RNA. Proc Natl Acad Sci USA 94:952-955.
(12) Zhang L, Zhou W, Velculescu V E, Kern S E, Hruban R H, Hamilton S R, Vogelstein B & Kinzler K W (1998) Gene expression profiles in normal and cancer cells. Science 276:1268-1272.
(13) Kinzler K W & Vogelstein B (1998) Cancer-susceptibility genes. Gatekeepers and caretakers. Nature 386:761-763.
(14) Parsonnet J (1995) Bacterial infection as a cause of cancer. Environ Health Perspect 103 Suppl 8:263-268.
(15) Williams M P & Pounder R E (1999) *Helicobacter pylori*: from benign to the malignant. Am J Gastroenterol 94: (11 Suppl): S11-16.
(16) Brown L M (2000) *Helicobacter pylori*: epidemiology and routes of transmission. Epidemiol Rev 22:283-297.

(17) Tarja A, et al. (15 authors) (2001) Serotypes of *Chlamydia trachomatis* and risk for development of cervical squamous cell carcinoma. JAMA 285:47-51.
(18) Macomber P B (1990) Cancer and cell wall deficient bacterial. Med Hypothesis 32:19.
(19) Cassell G H (1998) Infectious causes of chronic inflammation diseases and cancer. Emerg Infect Dis 4:475-487.
(20) El-Bayoumy K (1992) Environmental carcinogens that may be involved in human breast cancer etiology. Chem Res Toxicol 5:585-590.
(21) Sirbasku D A, Stewart B H, Pakala R, Eby J E, Sato H & Roscoe J M (1991) Purification of an equine apotransferrin variant (thyromedin) essential for thyroid hormone dependent growth of GHI rat pituitary tumor cells in chemically defined culture. Biochemistry 30:295-304.
(22) Sirbasku D A, Pakala R, Sato H & Eby J E (1991) Thyroid hormone-dependent pituitary tumor cell growth in serum-free chemically defined culture. A new regulatory role for apotransferrin. Biochemistry 30:7466-7477.
(23) Sirbasku D A, Pakala, R, Sato H & Eby J E (1991) Thyroid hormone regulation of rat pituitary tumor cell growth. A new role for apotransferrin as an autocrine thyromedin. Mol Cell Endocrinol 77:C47-C55. (A Cutting-Edge Article).
(24) Sato H, Eby J E & Sirbasku D A (1991) Iron is deleterious to hormone-responsive pituitary cell growth in serum-free defined medium. In Vitro Cell Dev Biol 27A:599-602.
(25) Sirbasku D A, Pakala R, Sato H & Eby J E (1992) Thyroid hormone and apotransferrin regulation of growth hormone secretion by GH1 rat pituitary tumor cells in iron restricted serum-free defined culture. In Vitro Cell Dev Biol 28A:67-71.
(26) Sato H, Eby J E, Pakala R & Sirbasku D (1992) Apotransferrins from several species promote thyroid hormone dependent rat pituitary tumor cell growth in iron restricted serum-free defined culture Mol Cell Endocrinol 83:239-251.
(28) Eby J E, Sato H & Sirbasku D A (1992) Preparation of iron deficient tissue culture medium by deferoxamine-Sepharose treatment and application to the differential actions of apotransferrin and diferric transferrin. Anal Biochem 203:317-325.
(28) Eby J E, Sato H & Sirbasku D A (1993) Apotransferrin stimulation of thyroid hormone dependent rat pituitary tumor cell growth in serum-free chemically defined medium: role of Fe (III) chelation. J Cell Physiol 156:588-600.
(29) Sirbasku, David A. "Compositions and Methods for the Diagnosis, Treatment and Prevention of Steroid Hormone Responsive Cancers" U.S. patent application Ser. No. 09/852,547 (U.S. Published Application No. 20020006630) and corresponding PCT Published Application No. WO 01/86307.
(30) Sirbasku, David A. "Compositions and Methods for Demonstrating Secretory Immune System Regulation of Steroid Hormone Responsive Cancer Cell Growth" U.S. patent application Ser. No. 09/852,958 (U.S. Published Application No. 20020012954 and corresponding PCT Published Application No. WO 01/85210.
(31) Zelada-Hedman M, et al (12 authors) (1998) A screening for BRCA1 mutations in breast and breast-ovarian cancer families from the Stockholm region. Cancer Res 57:2474-2477.
(32) Castilla L H et al (12 authors) (1994) Mutations in the BRCA1 gene in families with early onset breast and ovarian cancer. Nature Genetics 8:387-391.
(33) Biesecker M S et al (7 authors) (1993) Genetic counseling for families with inherited susceptibility to breast and ovarian cancer. JAMA 269:1970-1974.
(34) Sirbasku D A (1978) Hormone-responsive growth in vivo of a tissue culture cell line established from the MT-W9A rat mammary tumor. Cancer Res 38:1154-1165.
(35) Danielpour D & Sirbasku D A (1984) New perspectives in hormone-dependent (responsive) and autonomous mammary tumor growth: role of auto-stimulatory growth factors. In Vitro 20:975-980.
(36) El-Bayoumy K et al (7 authors) (1995) Comparative tumorgenicity of benzo[a]pyrene, 1-nitropyrene and 2-amino-1-methyl-6-phenylimidazo[4,5-b]pyridine administered by gavage to female CD rats. Carcinogenesis 16:4311-434.
(38) Russo 7, Tay L K & Russo I H (1982) Differentiation of the mammary gland and susceptibility to carcinogenesis. Breast Cancer Res Treat 2:5-73.
(38) Lieu P T, Heiskala M, Peterson P A & Yang Y (2001) The roles of iron in health and disease. Mol Aspects Med 22:1-87.
(39) Weinberg E D (1999) Iron therapy and cancer. Kidney Int Suppl 69:S131-S134.
(40) Weinberg E D (1996) The role of iron in cancer. Eur 7 Cancer Prevent 5:19-36.
(41) Dreicer R et al (7 authors) (1998) Phase II trial of deferoxamine in patients with hormone refractory metastatic prostate cancer. Cancer Invest 15:311-317.
(42) Brooks D et al (8 authors) (1995) Phase IA trial of murine immunoglobulin A anti-transferrin receptor antibody 42/6. Clin Cancer Res 1:1259-1265.
(43) Kemp J D et al (7 authors) (1992) Effects of anti-transferrin receptor antibodies on the growth of neoplastic cells. Pathobiology 60:27-32.
(44) Baselga J & Mendelsohn J (1994) Receptor blockade with monoclonal antibodies as anticancer therapy. Pharmacol Ther 64:127-154.
(45) McGregor D H et al (7 authors) (1978) Breast cancer incidence among atomic bomb survivors, Hiroshima and Nagaski 1950-1969. J Natl Cancer Inst 59:799-811.
(46) Cook K L, Adler D D, Lichter A F, Ikeda D M & Helvie M A (1990) Breast carcinoma in young women previously treated for Hodgkin's disease. Am J Roentgenol 155:39-42.
(47) Huggins C B (1988) Selective induction of hormone dependent mammary adenocarcinomas in the rat. J Lab Clin Med 109:262-266.
(48) Sinha D K, Pazik J E & Dao T L (1983) Progression of rat mammary development with age and its relationship to carcinogenesis by a chemical carcinogen. Int J Cancer 31:321-327.
(49) Schull J D, Spady T J, Snyder M C, Johansson S L & Pennington K L (1998) Ovary-intact, but not ovariectomized female ACI rats treated with 17β-estradiol rapidly develop mammary carcinoma. Carcinogenesis 18:1595-1601.
(50) McBurney M I, Van Soest P J & Jeraci J L (1988) Colon carcinogenesis: the microbial feast or famine mechanism. Nutr Cancer 10:23-28.
(51) Zarkobic M et al (7 authors) (1993) Tumor promotion by fecapentaene-12 in a rat colon carcinogenesis model. Carcinogenesis 14:1261-1264.
(52) Sosa R & Baness L (1988) Bacterial growth in human milk. Am J Dis Child 141:111-112.
(53) Murphy J F, Lewarne V M, Lowe G H & Howells C H L (1982) The provision of safe unpasteurized breast milk using a simple aseptic technique. J Infect 5:133-137.

(54) Igumbor E O, Mukura R D, Makandiramba B & Chihota V (2000) Storage of breast milk: effect of temperature and storage duration on microbial growth. Cent Afr J Med 46:247-251.

(55) Thompson N, Pickler R H, Munro C & Shotwell J (1998) Contamination in expressed breast milk following breast cleansing. J Human Lact 13:127-130.

(56) Martin F L et al (9 authors) (2000) DNA damage in human breast milk cells and its induction by early and late milk extracts. Carcinogenesis 21:799-804.

(57) Martin F L et al (7 authors) (1999) Genotoxicity of human milk extracts and detection of DNA damage in exfoliated cells recovered from breast milk. Biochem Biophys Res Commun 259:319-326.

(58) Martin F L et al (7 authors) (1996) Genotoxicity of human mammary lipid. Cancer Res 56:5342-5346.

(59) Uibu J, Tauts O, Levin A, Shimanovskaya N & Matto R (1996) N-nitroso-dimethylamine, nitrate and nitrate-reducing microorganisms in human milk. Acta Paediatr 85:1140-1142.

(60) Hoffmann F A, Sawatzki G, Schmitt H & Kubanek B (1982) A milker for mice. Lab Animal Sci 32:387-388.

(61) Fredricks D N & Relman D A (1999) Paraffin removal from tissue sections for digestion and PCR analysis. BioTechniques 26:198-200.

(62) Relman D A (1998) Detection and identification of previously unrecognized microbial pathogens. Emerg Infect Dis 4:382-389.

(63) Wagar E A (1996) Defining the unknown: molecular methods for finding new microbes. J Clin Lab Anal 10:331-334.

(64) Relman D A (1999) The search for unrecognized pathogens. Science 284:1308-1310.

(65) Fredricks D N & Relman D A (1999) Application of polymerase chain reaction to the diagnosis of infectious diseases. Clin Infect Dis 29:475-486.

(66) Ames B N (1979) Identifying environmental chemicals causing mutations and cancer. Science 204:587-593.

(67) Hill D C, Rigley S K & Nesbit U (1998) Novel screen methodology for identification of new microbial metabolites with pharmacological activity. Adv Biochem Eng BioTechnol 59:73-121.

(68) Bogen K T (1995) Improved prediction of carcinogenic potencies from mutagenic potencies for chemicals positive in rodents and the Ames Test. Environ Mol Mutagen 25:37-49.

(69) Kim B S & Margolin B H (1999) Statistical methods for the Ames *Salmonella* assay: a review. Mutagenesis Res 436:113-122.

(70) Slamon D J et al. (12 authors) (2001) Use of chemotherapy plus monoclonal antibody against HER2 for metastatic breast cancer that overexpresses HER2. N Eng J Med 344:783-792.

(71) Karey K P & Sirbasku D A (1988) Differential responsiveness of the human breast cancer cell lines MCF-7 and T47-D to growth factors and 17β-estradiol. Cancer Res 48:4083-4092.

(72) Ogasawara M & Sirbasku D A (1988) A new serum-free method of measuring growth factor activities for human breast cancer cells in culture. In Vitro Cell Dev Biol 24:911-920.

(73) Nocka K H & Pelus L M (1988) Cell cycle specific effects of deferoxamine on human and murine hematopoietic progenitor cells. Cancer Res 48:3571-3575.

(74) Hoffbrand A V, Ganeshaguru K, Hooton J W & Tattersall M H (1976) Effect of iron deficiency and desferrioxamine on DNA synthesis in human cells. Br J Haematol 33:517-526.

(75) Spiro T G, Allerton S E, Renner J, Terzis A, Bils R & Saltman P (1966) The hydrolytic polymerization of iron (III). J Amer Chem Soc 88:2721-2726.

(76) Colditz G A (1993) Epidemiology of breast cancer. Findings from the nurses' health study. Cancer 71:1480-1489.

(77) Kelsey J L & Gammon M D (1990) Epidemiology of breast cancer. Epidemiologic Rev 12:228-240.

(78) Kelsey J L & Gammon M D (1991) The epidemiology of breast cancer. CA Cancer Journal for Clinicians 41:157.

(79) Jordan V C (2000) Progress in the prevention of breast cancer: concept to reality. J Steroid Biochem Mol Biol 74:269-277.

(80) Hoffmann J S & Cazaux C (1998) DNA synthesis, mismatch repair and cancer. Int J Onocol 12:377-382.

(81) Minnick D T & Kunkel T A (1996) DNA synthesis errors, mutators and cancer. Cancer Surv 28:3-20.

(82) Ames B N, Gold L S & Willet W C (1995) The causes and prevention of cancer. Proc Natl Acad Sci USA 92:5258-5268.

(83) Albanes D & Winick M (1988) Are cell number and cell proliferation risk factors for cancer? J Natl Cancer Inst 80:772-775.

(84) Preston-Martin S, Pike M C, Ross R K, Jones P A & Henderson B E (1990) Cancer Res 50:7415-7421.

(85) Olsson H (2000) Tumour biology of a breast cancer at least partly reflects the biology of the tissue/epithelial cell origin at the time of initiation—a hypothesis. J Steroid Biochem Mol Biol 74:345-350.

(86) Rosen P P (1979) The pathological classification of human mammary carcinoma: past, present and future. Ann Clin Lab Sci 9:144-156.

(87) Russo J, Hu Y-F, Yang X & Russo I H (2000) Chapter 1: Developmental, cellular, and molecular basis of human breast cancer. J Natl Cancer Inst Monographs No. 27:17-37.

(88) (News Article) Nelson N J (1998) Cancer risk high, but lower than expected with breast cancer genes. J Natl Cancer Inst 89:28-29.

(89) Krainer M et al (12 authors) (1998) Differential contributions of BRCA1 and BRCA2 to early-onset breast cancer. N Eng J Med 336:1416-1421. Comment in: N Eng J Med (1998) 336:1448-1449.

(90) Couch F J et al (9 authors) (1998) BRCA1 mutations in women attending clinics that evaluate the risk of breast cancer. 336:1409-1415. Comments in: N Eng J Med (1998) 336:1448-1449.

(91) Struewing J P et al (9 authors) (1998) The risk of cancer associated with specific mutations of BRCA1 and BRCA2 among Ashkenazi Jews. N Eng J Med 336:1401-1408. Comments in: N Eng J Med (1998) 336:1448-1449; N Eng J Med (1998) 337:788-789.

(92) Elledge R M, Fuqua S A W, Clark G M, Pujol P & Allred D C (1993) The role and prognostic significance of p53 gene alterations in breast cancer. Breast Cancer Res Treat 27:95-102.

(93) Elledge R M & Allred D C (1994) The p53 tumor suppressor gene in breast cancer. Breast Cancer Res Treat 32:39-47.

(94) Coles C, et al (6 authors) (1992) p53 mutations in breast cancer. Cancer Res 52:5291-5298.

(95) Wakabayashi K, Nagao M, Esumi H & Sugimura T (1992) Food-derived mutagens and carcinogens. Cancer Res 52:2092s-2098s.

(96) Berg J (1999) Clinical studies of p53 in treatment and benefit of breast cancer patients. Endocr Relat Cancer 6:51-59.

(97) Oesterreich S & Fuqua S A (1999) Tumor suppressor genes in breast cancer. Endocr Relat Cancer 6:405-419.

(98) Hamilton A & Piccart M (2000) The contribution of molecular markers to the prediction of response in the treatment of breast cancer: a review of the literature on HER-2, p53 and BCL-2. Ann Oncol 11:647-663.

(99) Wolf M S & Weston A (1998) Breast cancer risk and environmental exposures. Environ Health Perspect 105 (Suppl):891-896.

(100) Cahill D P, Kinzler K W. Vogelstein B & Lengauer C (1999) Genetic instability and darwinian selection in tumours. Trends Cell Biol 9:M57-M60.

(101) Loeb L A (1994) Microsatellite instability: marker of a mutator phenotype in cancer. Cancer Res 54:5059-5063.

(102) Gruber S B, Petersen G M, Kinzler K W & Vogelstein B (1999) Cancer, crash sites, and the new genetics of neoplasia. Gastroenterology 116:210-212.

(103) Mirsky S (2001) A host with infectious ideas. Sci Am 284:32-33.

(104) Rosenblatt K A, Wicklund K G & Stanford J L (2001) Sexual factors and the risk of prostate cancer. Am J Epidemiol 153:1152-1158.

(105) Hartmann A, Blaszyk H, Kovach J S & Sommer S S (1998) The molecular epidemiology of p53 gene mutations in human breast cancer. Trends Genet 13:27-33.

(106) Wiseman R A (2000) Breast cancer hypothesis: a single cause for the majority of cases. J Epidemiol Community Health 54:851-858.

(107) Yager J D (2000) Chapter 3: Endogenous estrogens as carcinogens through metabolic activation. J Natl Cancer Inst Monographs 2000 No. 27:67-73.

(108) Cavalieri E, Frenkel K, Liehr J G, Rogan E & Roy D (2000) Chapter 4: Estrogens as endogenous genotoxic agents—DNA adducts and mutations. J Natl Cancer Inst Monographs 2000 No. 27:75-94.

(109) Dickson R B & Stancel G M (2000) Estrogen receptor-mediated processes in normal and cancer cells. J Natl Cancer Inst Monographs 2000 No. 27:135-145.

(110) Sirbasku D A & Moreno-Cuevas J E (2000) Estrogen mitogenic action. II. Negative regulation of the steroid hormone-responsive growth of cell lines derived from human and rodent target tissue tumors and conceptual implications. In Vitro Cell dev Biol 36:428-446.

(111) Beckmann M W, Niedderacher D, Schnurch H G, Gusterson B A & Bender H G (1998) Multistep carcinogenesis of breast cancer and tumour heterogeneity. J Mol Med 75:429-439.

(112) Parsons R (1999) Oncogenetic basis of breast cancer. In: Breast cancer, Roses D F (ed), Churchill Livingstone, New York, N.Y., pp 13-23.

(113) Sato, G. H., Pardee, A. B., and Sirbasku, D. A. (Volume Editors), Cold Spring Harbor Conferences on Cell Proliferation, Volume 9, Books A and B, Growth of Cells in Hormonally Defined Media. Cold Spring Harbor, N.Y., 1982.

(114) Barnes, D. W., Sirbasku, D. A., and Sato, G. H. (Volume Editors), Cell Culture Methods for Molecular and Cell Biology. Volume 1, Methods for Preparation of Media, Supplement and Substrata for Serum-free Animal Cell Culture, Alan R. Liss/John Wiley, New York, 1984.

(115) Barnes, D. W., Sirbasku, D. A., and Sato, G. H. (Volume Editors), Cell Culture Methods for Molecular and Cell Biology. Volume 2, Methods for Serum-free Culture of Cells of the Endocrine System, Alan R. Liss/John Wiley, New York, 1984.

(116) Barnes, D. W., Sirbasku, D. A., and Sato, G. H. (Volume Editors). Cell Culture Methods for Molecular and Cell Biology, Volume 3, Methods for Serum-free Culture of Epithelial and Fibroblastic Cells, Alan R. Liss/John Wiley, New York, 1984.

(117) Barnes, D. W., Sirbasku, D. A., and Sato, G. H. (Volume Editors). Cell Culture Methods for Molecular and Cell Biology, Volume 4, Methods for Serum-free Culture for Neuronal and Lymphoid Cells, Alan R. Liss/John Wiley, New York, 1984.

(118) Mason A B et al (10 authors) (1998) Receptor recognition sites reside in both lobes of human serum transferrin. Biochem J 326:77-85.

(119) Zalk O, Trinder D & Aisen P (1994) Primary receptor-recognition site of human transferrin is in the C-terminal lobe. J Biol Chem 269:7110-7114.

(120) Reif D W (1992) Ferritin as a source of iron for oxidation damage. Free Radical Biol Med 12:417-427.

(121) Higgy N A, Salicioni A M, Russo I H, Zhang P L & Russo J (1998) Differential expression of human ferritin H chain gene in immortal human breast epithelial MCF-10F cells. Mol Carcinogenesis 20:332-339.

(122) Kontoghioghes G J & Weinberg E D (1995) Iron: mammalian defense systems, mechanisms of disease, and chelation therapy approaches. Blood Rev 9:33-45.

(123) Weinberg E D (1994) Association of iron with colorectal cancer. Biometals 7:211-216.

(124) Weinberg E D (1992) Roles of iron in neoplasia. Promotion, prevention and therapy. Biol trace Elem Res 34:123-140.

(125) Weinberg E D (1986) Iron, infection, and neoplasia. 4:50-60.

(126) Theil E C (1988) Ferritin: structure, gene regulation, and cellular function in animals, plants and microorganisms. Annu Rev Biochem 56:289-315.

(127) Kawabata H, Yang R, Hirama T, Vuong P T, Kawano S, Gombart A F & Koeffler H P (1999) Molecular cloning of transferrin receptor 2. A new member of the transferrin receptor-like family. J Biol Chem 274:20826-20832.

(128) Trowbridge I S & Shackelford D A (1986) Structure and function of transferrin receptors and their relationship to cell growth. Biochem Soc Symp 51:117-129.

(129) Gatter K C, Brown G, Trowbridge I S, Woolston R E & Mason D Y (1983) Transferrin receptors in human tissues: their distribution and possible clinical significance. J Clin Pathol 36:539-545.

(130) Anison P (1982) Current concepts in iron metabolism. Clin Lab Haematol 11:241-257.

(131) Reichard P & Ehrenberg A (1983) Ribonucleotide reductase—a radical enzyme. Science 221:514-519.

(132) Nunez M-T & Glass J (1983) The transferrin cycle and iron uptake in rabbit reticulocytes. Pulse studies using $^{59}$Fe, $^{125}$I-labeled transferrin. J Biol chem. 258:9676-9680.

(133) Ciechanover A, Schwartz A L, Dautry-Varsat A & Lodish H F (1983) Kinetics of internalization and recycling of transferrin and the transferrin receptor in a human hepatoma cell line. J Biol Chem 258:9681-9689.

(134) Defter M C, Yvonne Jones E (2000) Cell surface receptors. Curr Opin Struct Biol 10:213-219.

(135) Barnes D & Sato G (1980) Methods for growth of cultured cells in serum-free medium. Anal Biochem 102: 255-270.

(136) Aisen P, Liebman A & Zweier J (1978) Stoichiometric and site characteristics of the binding of iron to human transferrin. J Biol Chem 253:1930-1937.

(137) Physicians' Desk Reference, PDR 55th Edition, 2001, InfeD® (Iron Dextran Injection, USP), pp 2879-2881.

(138) Jin Y, Baquet A, Florence A, Crichton R R, Schneider Y-J (1989) Desferrithiocin and desferrioxamine B. Cellular pharmacology and storage iron mobilization. Biochem Pharmacol 38:3233-3240.

(139) Liehr J G & Jones J S (2001) Role of iron in estrogen-induced cancer. Curr Med Chem 8:839-849.

(140) Thompson H J, Kennedy K, Witt M & Juzefy J (1991) Effect of dietary iron deficiency or excess on the induction of mammary carcinogenesis by 1-methyl-1-nitrosourea. Carcinogenesis 12:111-114.

(141) Webster D J (1981) Tumour induction by carcinogens in iron deficient rats. Anticancer Res 1:293-294.

(142) Riss T L & Sirbasku D A (1988) Purification and identification of transferrin as a major pituitary derived mitogen for MTW9/PL2 rat mammary tumor cells. In Vitro Cell Dev Biol 23:841-849.

(143) Danielpour D, Riss T L, Ogasawara M & Sirbasku D A (1988) Growth of MTW9/PL2 estrogen-responsive rat mammary tumor cells in hormonally defined serum-free media. In Vitro Cell Dev Biol 24:42-52.

(144) Kontoghiorghes G J & Evans R W (1985) Site specificity of iron removal from transferrin by α-ketohydroxypyridine chelators. FEBS Letters 189:141-144.

(145) Spicer D V & Pike M C, Chapter 5: Risk factors. Breast Cancer, Roses D F (ed), Churchill Livingstone, New York, N.Y., 1999, pp 47-54.

(146) Nathavitharana K A, Catty D & McNeish A S (1994) IgA antibodies in human milk: epidemiology markers of previous infections? Arch Dis Child Fetal Neonatal Ed 71:F192-197.

(147) Nathavitharana K A, Catty D, Raykundalia C & McNeish A S (1995) Presence of secretory IgA antibodies to an enteric bacteria pathogen in human milk and saliva. Arch Dis Child Fetal Neonatal Ed 72:F102-106.

(148) Ahlstedt S, Carlsson B, Hanson L A & Goldblum R M (1975) Antibody production by human colostrum cell. I. Immunoglobulin class, specificity, and quantity. Scand J Immunol 4:535-539.

(149) Goldblum R M, Ahlstedt S, Carlsson B, Hanson A L, Jodal U, Lidin-Janson G & Sohl-Ackerlund A (1975) Antibody-forming cells in human colostrum after oral administration. Nature 257:797-799.

(150) Kozlowski P A, Cu-Uvin S, Neutra M R & Flanigan T P (1998) Comparison of the oral, rectal, and vaginal immunixation routes for induction of antibodies in rectal and genital tract secretions of women. Infect Immun 65:1387-1394.

(151) Tracket C O, Mason H S, Losonsky G, Estes M K, Levine M M & Arntzen C J (2000). Human immune responses to a novel Norwalk virus vaccine delivered in transgenic potatoes. J Infect Dis 182:302-305.

(152) Arakawa T, Chong D K & Langridge W H (1998) Efficacy of a food plant-based oral cholera toxin B subunit vaccine. Nat BioTechnol 16:292-297. Erratum in: Nat Biotechnol 16:478.

(153) Pierce N F & Gowans J L (1975) Cellular kinetics of the intestinal immune response to cholera toxoid in rats. J Exp Med 142:1550-1563.

(154) Del Giudice G, Pizza M & Rappuoli R (1999) Mucosal delivery of vaccines. Methods 19:148-155.

(155) Tracket C O & Mason H S (1999) A review of oral vaccination with transgenic vegetables. Microbes Infect 1:777-783.

(156) Fielding J (1978) Does sarcoma occur in man after intramuscular iron? Scand J Haematol Suppl 32:100-104.

(157) Magnusson G, Floodh H & Malmfors T (1978) Onocological study of Ferastral, an iron-poly-(sorbitol-gluconic acid) complex, after intramuscular administration. Scand J Haematol Suppl 32:87098.

(158) Greenberg G (1976) Sarcomata have developed after intramuscular infection of iron. Br Med J 1: 1508-1509.

(159) Robertson A G & Dick W C (1978) Intramuscular iron and local oncogenesis. Br J Med 1:946.

(160) Weinberg E D, Saim R & Greenberg G (1978) Intramuscular injections of iron compounds and oncogenesis in man. Br Med J 1:683-685.

(161) Kumpf V J & Holland E G (1990) Parenteral iron dextran therapy. DICP 24:162-166.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. For example, the foregoing discussion specifically focuses on the eradication of breast cancer, however the same or similar approaches can be employed to eradicate other types of cancers of mucosal tissues, including prostate, ovary, endometrium, cervix, vagina, colon, kidney, lung and nasopharynx. Cancers of those tissues, together with breast cancer, account for 80% of all human cancer. The disclosures of all patents, patent applications and publications cited above are hereby incorporated herein by reference. The discussion of certain references in the Description of Related Art, above, is not an admission that they are prior art to the present invention, especially any references that may have a publication date after the priority date of this application.

What is claimed is:

1. A method to aid in deterring the occurrence, growth or progression of breast cancer in a population of susceptible individuals, the method comprising:

identifying individuals having a localized tumor or mastectomy or lumpectomy site including ER+ breast cancer cells, administering locally to said localized tumor or mastectomy or lumpectomy site in said identified individuals a pharmaceutically acceptable form of a source of iron in a suitable carrier, wherein said source of iron comprises Fe(II), Fe(III), radioactive Fe(II) or Fe(III), or Fe(III)-bound transferrin or apotransferrin molecules that are also bound to another radioactive metal, wherein the iron in said source of iron is present at a concentration sufficient to kill at least a portion of the ER+ breast cancer cells in said tumor or at said mastectomy or at said lumpectomy site.

2. A method of treating ER+ breast cancer cells comprising:

administering locally to a tumor site including ER+ breast cancer cells of a source of iron, wherein the source of iron is one or more sources selected from the group consisting of: iron (III) and/or iron (II) ions, $^{59}$Fe-transferrin or $^{55}$Fe-transferrin complexes, and $^{59}$Fe-deferoxamine-sepharose complex; and wherein the iron in said source of iron is present at a concentration sufficient to kill at least a portion of the ER+ breast cancer cells.

3. The method of claim 2, wherein the source of iron is a source of iron (III) and/or iron (II) ions, and the iron (III) and/or iron (II) ion concentration in the source is in a range from between about 10 micromolar to about 50 micromolar.

4. The method of claim 2 further comprising:
monitoring the effectiveness of the treatment; and
adding an iron ion chelator to terminate treatment.

5. The method of claim 4, wherein the iron ion chelator is selected from the group consisting of deferoxamine, EDTA, and citrate.

6. The method of claim 2 further comprising administering a metal-transferrin complex having a radiolabeled metal.

7. The method of claim 6, wherein the radiolabeled metal is selected from the group consisting of $^{59}$Fe and $^{55}$Fe.

8. The method of claim 2, wherein said source of iron is a source of iron (III) and/or iron (II) ions, and said administering of said source of iron (III) or iron (II) is followed by performing surgery to remove said tumor.

9. The method of claim 2 wherein said source of iron is a source of iron (III) or iron (II) ions, and further comprising applying said source of iron(III) or iron (II) to a mastectomy or lumpectomy site.

10. The method of claim 2 wherein said source of iron is a source of iron (III) or iron (II) ions, and further comprising applying said source of iron(III) or iron (II) to surgical margins of a mastectomy or lumpectomy site.

11. The method of claim 2, wherein said source of iron is a source of iron (III), and wherein said iron (III) ion is selected from the group consisting of ferric ammonium citrate, ferric ammonium sulfate, ferric chloride, ferric nitrate, ferric sulfate, ferric nitrate hydroxide, and combinations thereof.

12. The method of claim 2, wherein the source of iron is a source of iron (III) and/or iron (II) ions, and wherein said iron (III) and/or iron (II) ions comprise radiolabeled $^{59}$Fe or $^{55}$Fe.

13. The method of claim 12, wherein said radiolabeled $^{59}$Fe or $^{55}$Fe is disposed within or conjugated to an insoluble matrix.

14. The method of claim 13, wherein said insoluble matrix comprises non-biodegradable implantable beads.

15. The method of claim 13, wherein said insoluble matrix is selected from the group consisting of dextran, starch, and sepharose.

16. The method of claim 2, wherein said source of iron is a source of iron (III) and/or iron (II) ions, and wherein the source of iron (III) and/or iron (II) ions is administered in a biodegradable polymer.

17. The method of claim 16, wherein said biodegradable polymer is selected from the group consisting of dextran, starch, and sepharose.

18. A method of treating ER+ breast cancer cells comprising:
administering locally to a tumor site a source of iron (III) and/or iron (II) ions, wherein the tumor site includes ER+ breast cancer cells; and wherein the iron (III) and/or iron (II) ion concentration effective for killing said breast cancer cells is in a range from between about 1 micromolar to about 50 micromolar; and
administering locally to a tumor site a metal-transferrin complex having a radiolabeled metal.

19. The method of claim 2 in which the source of iron is a source of iron (III) ions and/or iron (II) ions.

20. The method of claim 19 in which the source of iron is a source of iron (II) ions.

21. The method of claim 19 in which the source of iron is a source of iron (III) ions.

22. The method of claim 21 which comprises administering the source of iron (III) ions to ER+ breast cancer cells.

23. The method of claim 21 in which the iron (III) ions comprise $^{55}$Fe and/or $^{59}$Fe.

24. The method of claim 23 in which the iron (III) ions comprise $^{59}$Fe.

25. The method of claim 21 in which the iron (III) ions comprise non-radioactive iron (III) ions.

26. The method of claim 25 and which further includes administering a source of $^{59}$Fe iron (III) ions.

27. The method of claim 26 wherein the $^{59}$Fe is disposed within or conjugated to an insoluble matrix.

28. The method of claim 27 wherein the insoluble matrix is selected from the group consisting of dextran, starch and sepharose.

29. The method of claim 25 which further includes administering a metal-transferrin complex having a radiolabeled metal.

30. The method of claim 29 wherein the radiolabeled metal is selected from the group consisting of $^{59}$Fe and/or $^{55}$Fe.

31. The method of claim 30 in which the radiolabeled metal is $^{59}$Fe.

32. The method of claim 1 comprising administering to an individual an effective amount of Fe(III) ions.

33. The method of claim 32 and further comprising administering to the individual $^{59}$Fe-transferrin and/or $^{55}$Fe-transferrin complexes.

34. The method of claim 33 which comprises administering to the individual $^{59}$Fe transferrin complexes.

35. The method of claim 32 and further comprising administering to the individual $^{59}$Fe-deferoxamine.

36. The method of claim 35 which comprises administering to the individual a $^{59}$Fe-deferoxamine-sepharose complex.

* * * * *